United States Patent [19]

Breslow et al.

[11] 4,252,719

[45] Feb. 24, 1981

[54] STEROID CONVERSION METHOD AND PRODUCTS PRODUCED THEREBY

[75] Inventors: Ronald C. D. Breslow, Englewood; Richard J. Corcoran, Maywood; Barry B. Snider, Princeton, all of N.J.

[73] Assignee: Research Corporation, New York, N.Y.

[21] Appl. No.: 934,314

[22] Filed: Aug. 17, 1978

Related U.S. Application Data

[63] Continuation of Ser. No. 786,060, Apr. 8, 1977, abandoned, which is a continuation of Ser. No. 621,163, Oct. 9, 1975, abandoned.

[51] Int. Cl.² ............................................. C07J 71/00
[52] U.S. Cl. .................... 260/239.55 D; 260/397.2; 260/397.4; 260/397.47; 260/397.5; 260/397.1; 260/397.45

[58] Field of Search .................. 260/239.55 D, 397.4, 260/397.45, 397.5

[56] References Cited

U.S. PATENT DOCUMENTS 4,061,661  12/1977  Kerb et al. ...................... 260/397.45

Primary Examiner—Elbert L. Roberts
Attorney, Agent, or Firm—Cooper, Dunham, Clark, Griffin & Moran

[57] ABSTRACT

Method for the removal of selected tertiary hydrogen atoms from 5 α-steroids of the cholestane, androstane and pregnane series by chlorination of 5 α-steroids esterified with selected iodoaryl substituted esterifying agents which direct a chlorine atom from the chlorinating agent into reactive proximity to the hydrogen atom to be removed.

24 Claims, No Drawings

CHART A
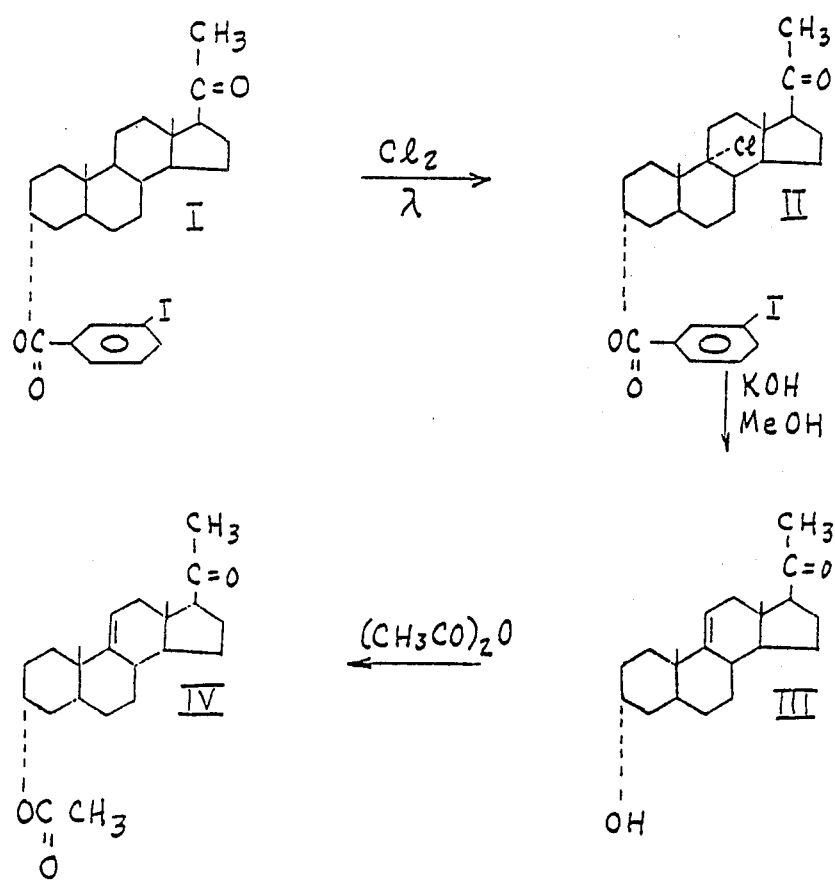

CHART B
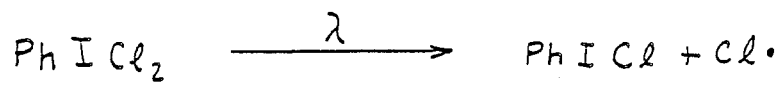
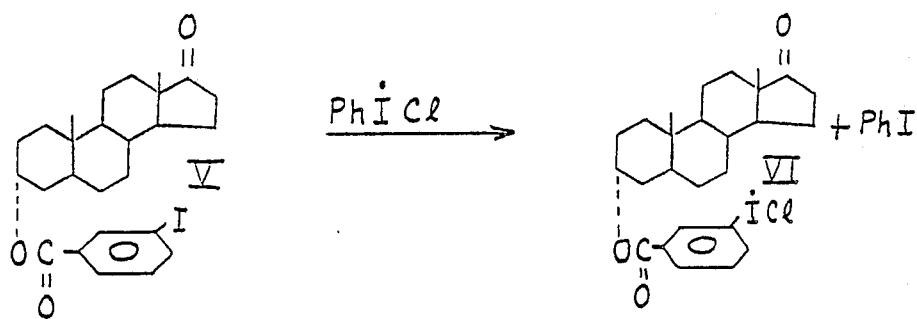
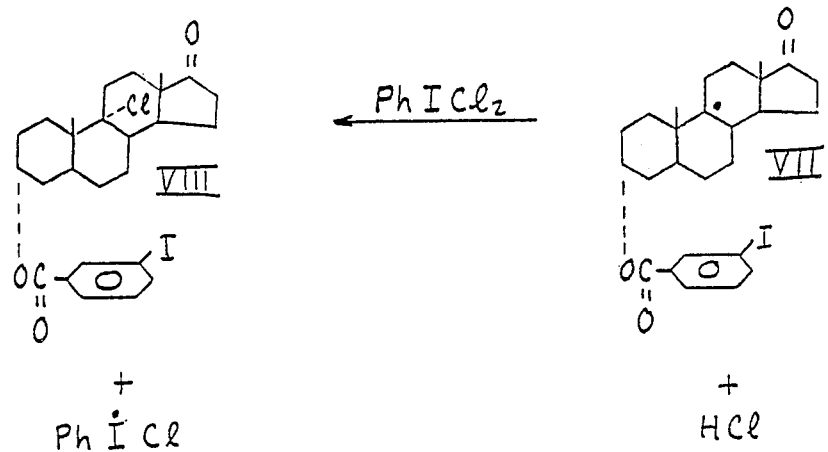

CHART C
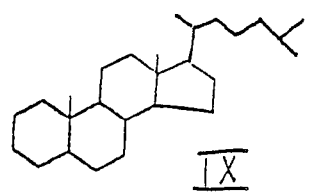
IX
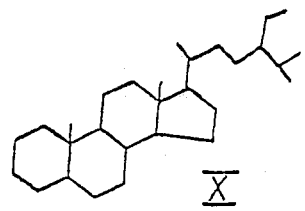
X
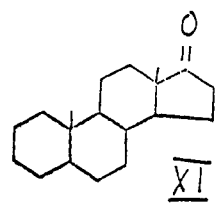
XI
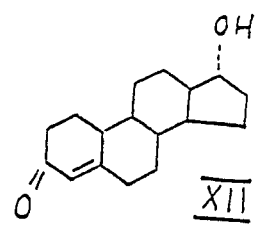
XII
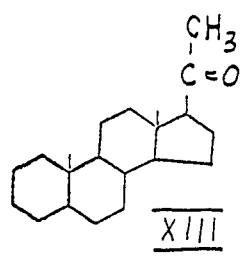
XIII
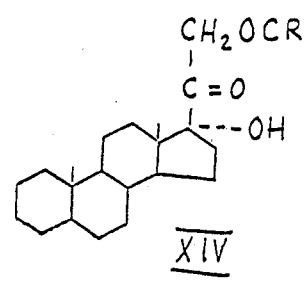
XIV
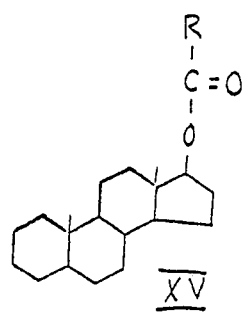
XV
XVI CHART D
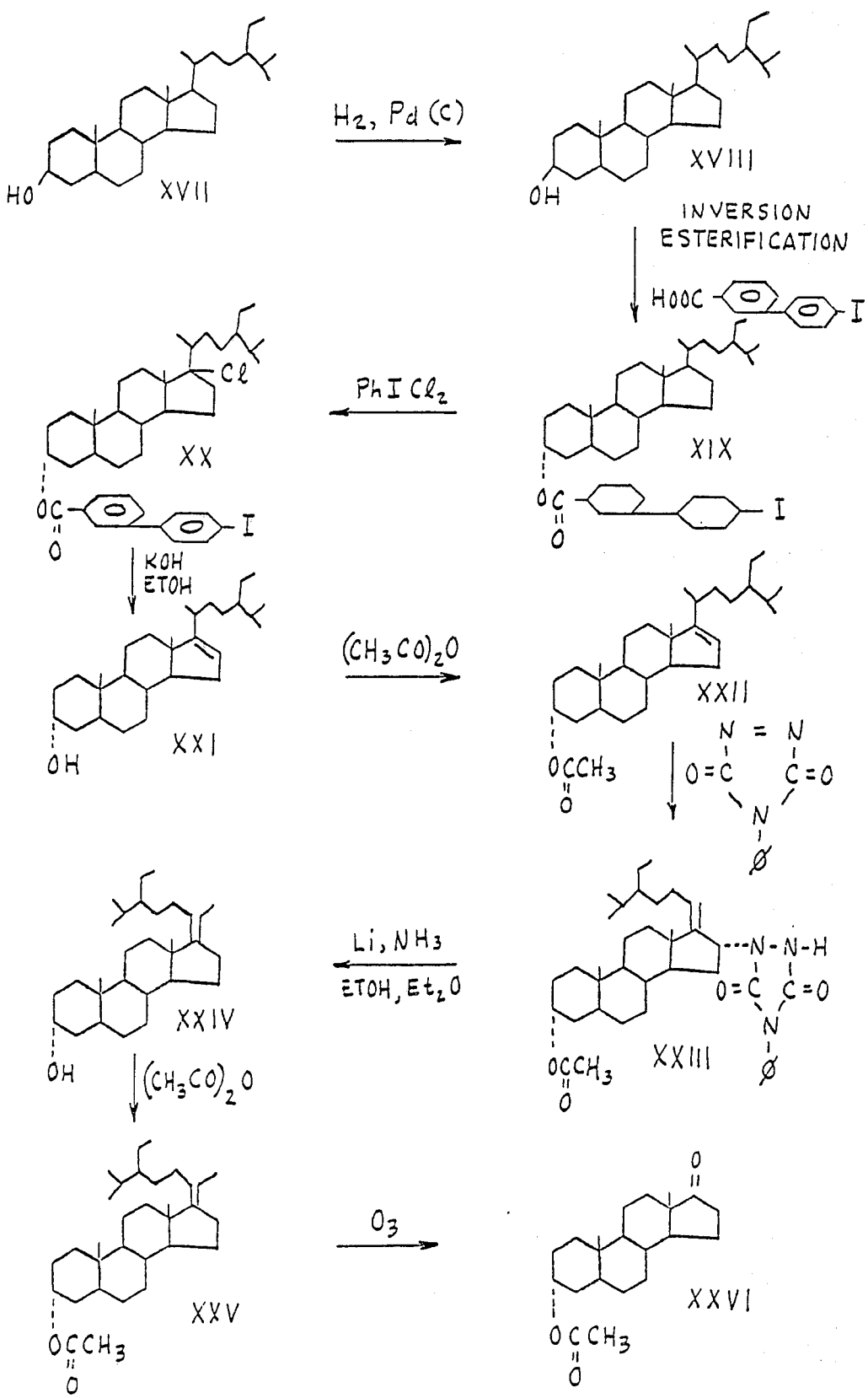

CHART E
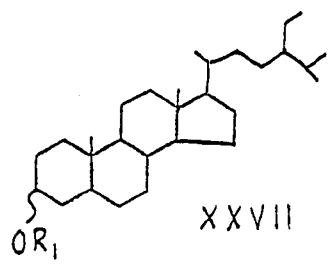 XXVII
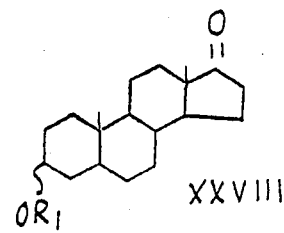 XXVIII
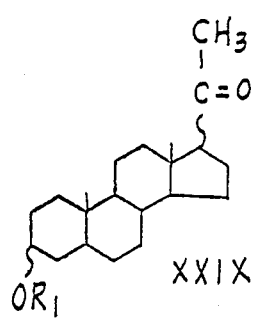 XXIX
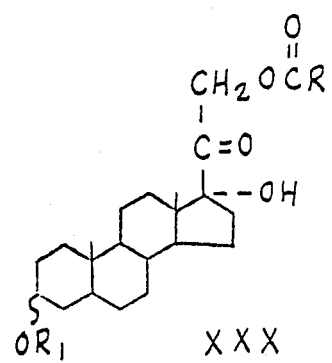 XXX
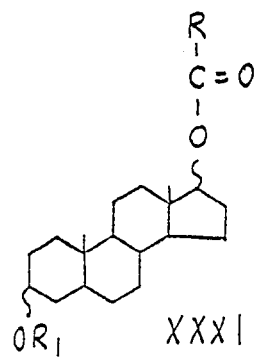 XXXI
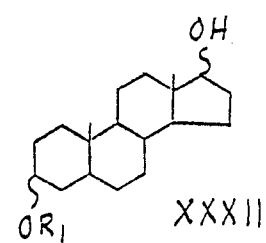 XXXII CHART F
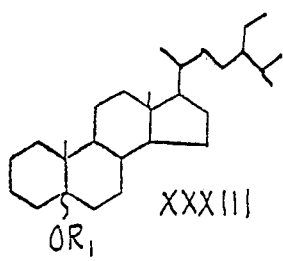 XXXIII
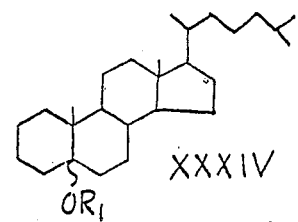 XXXIV
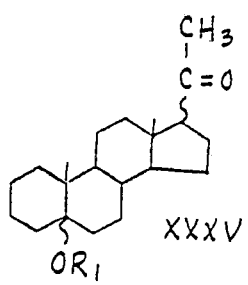 XXXV
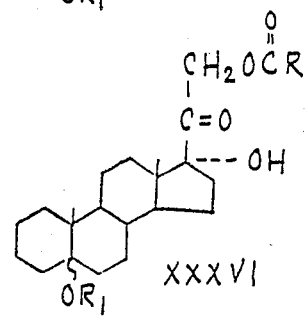 XXXVI
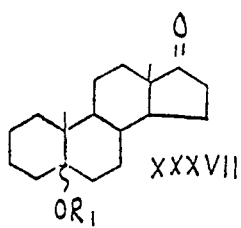 XXXVII
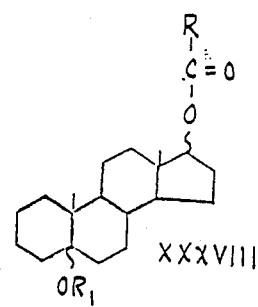 XXXVIII
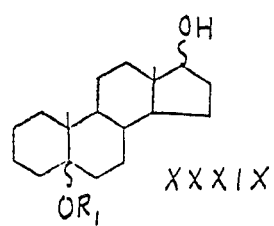 XXXIX CHART G
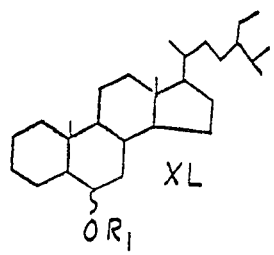
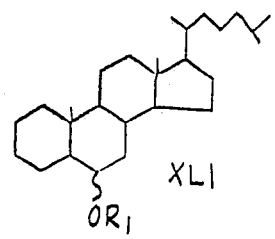
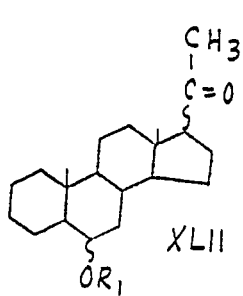
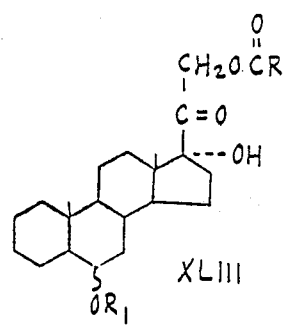
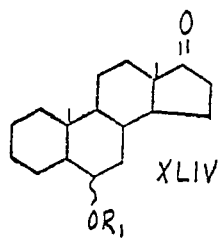
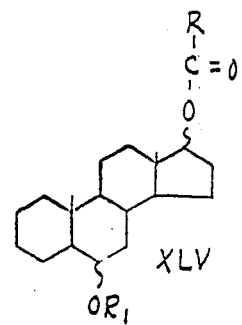
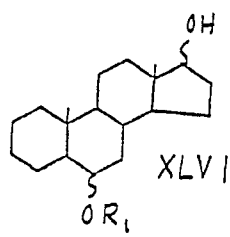

CHART H
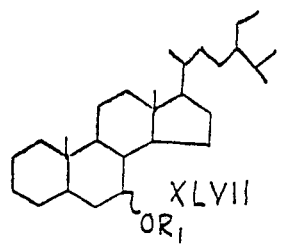
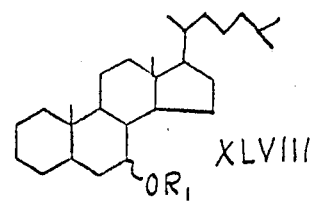
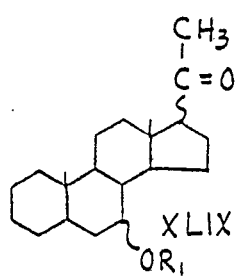
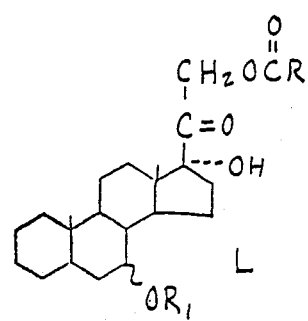
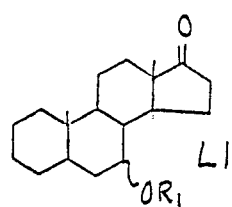
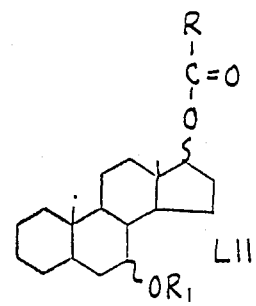
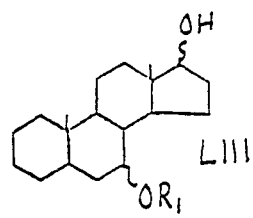

CHART J
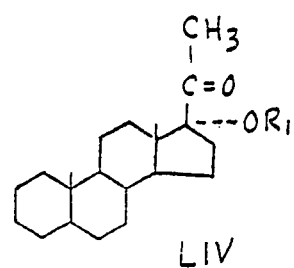
LIV
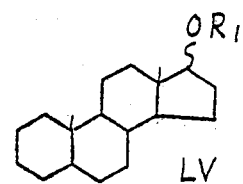
LV
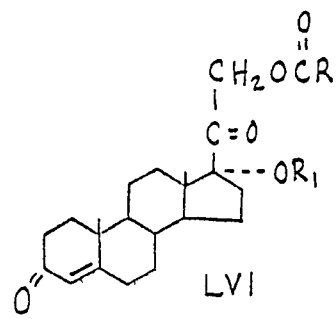
LVI
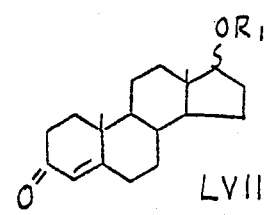
LVII

CHART K
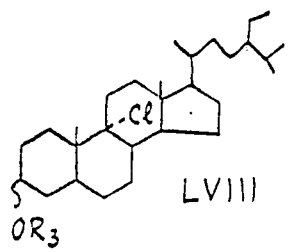 LVIII
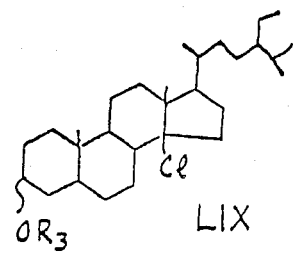 LIX
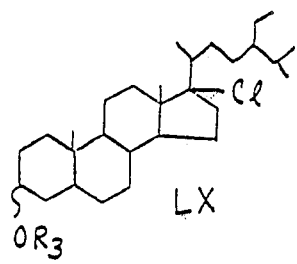 LX
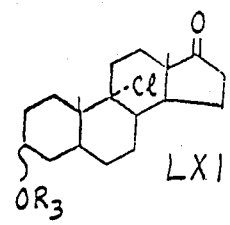 LXI
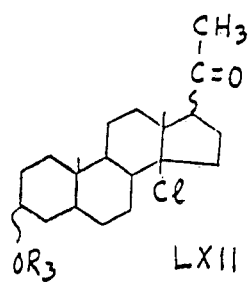 LXII
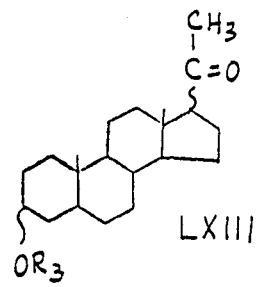 LXIII
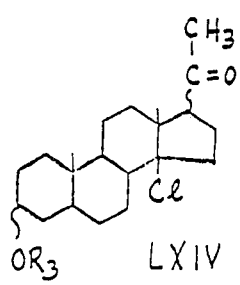 LXIV
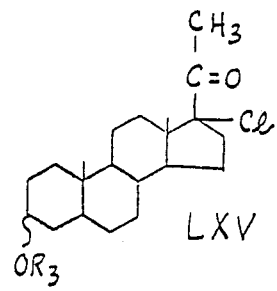 LXV
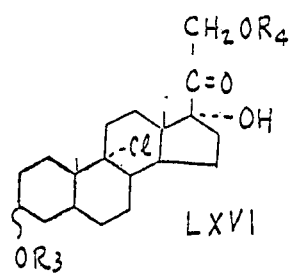 LXVI

CHART K CONTINUED
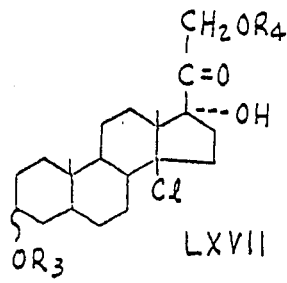
LXVII
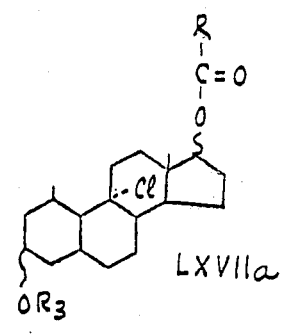
LXVIIa
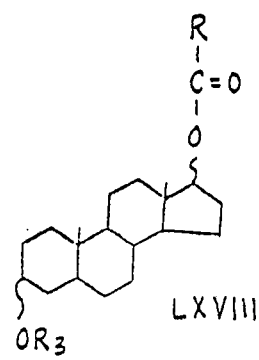
LXVIII
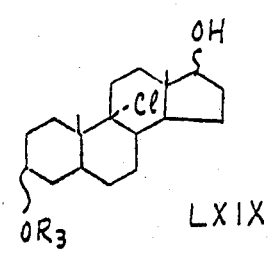
LXIX
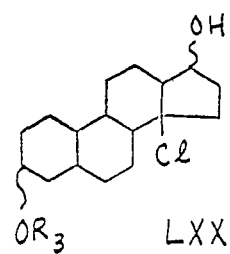
LXX CHART L
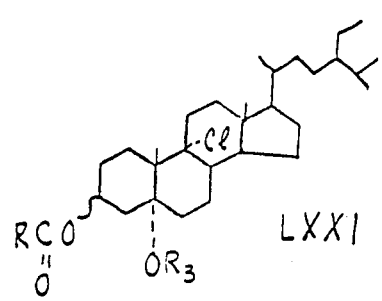 LXXI
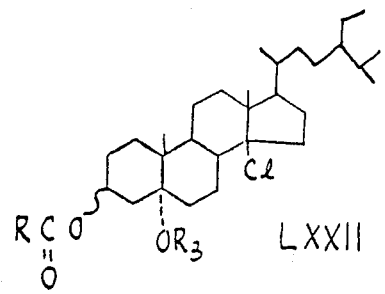 LXXII
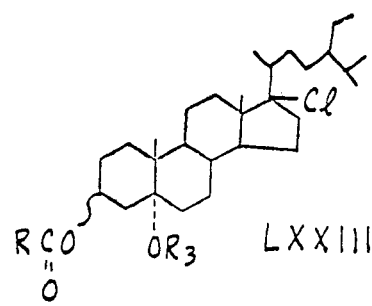 LXXIII
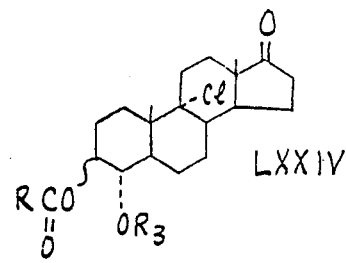 LXXIV
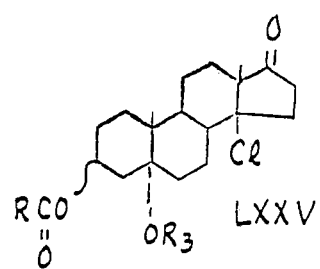 LXXV
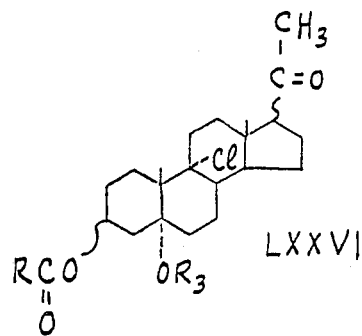 LXXVI
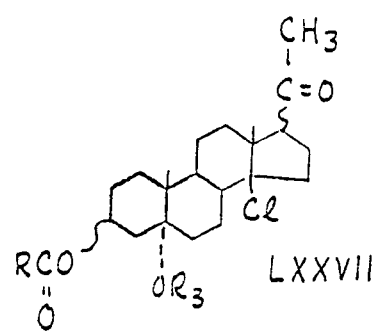 LXXVII
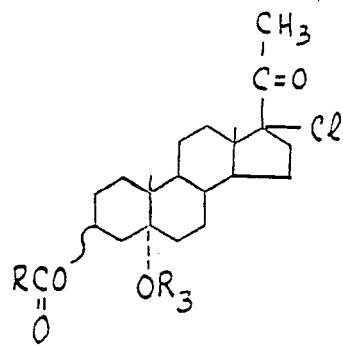

CHART L CONTINUED (1)
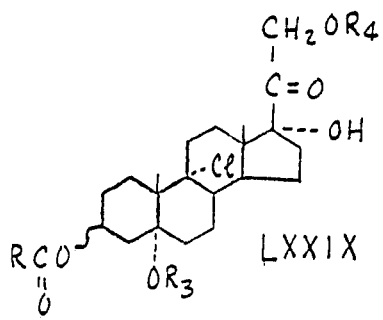 LXXIX
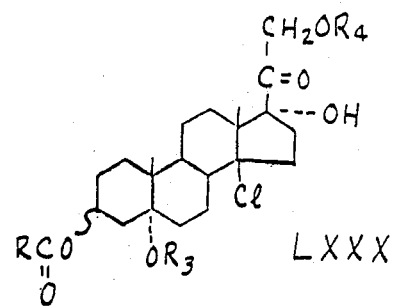 LXXX
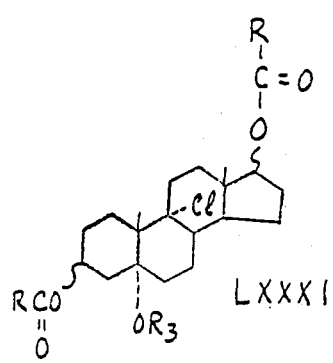 LXXXI
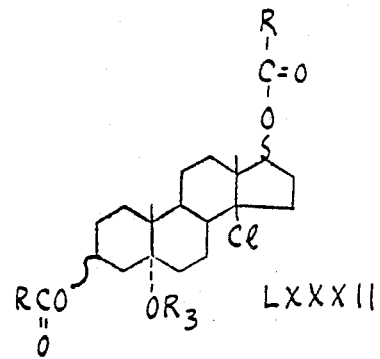 LXXXII
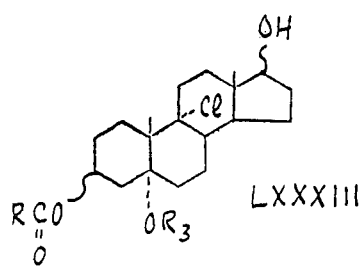 LXXXIII
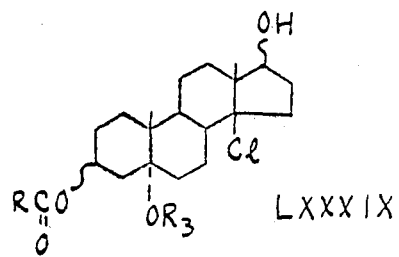 LXXXIX CHART L CONTINUED (2)
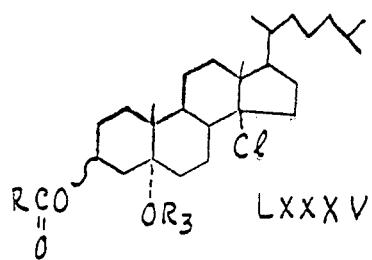 LXXXV
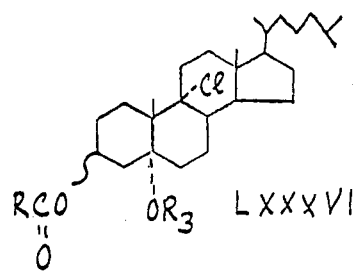 LXXXVI
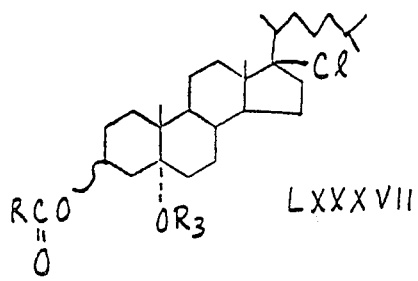 LXXXVII CHART M
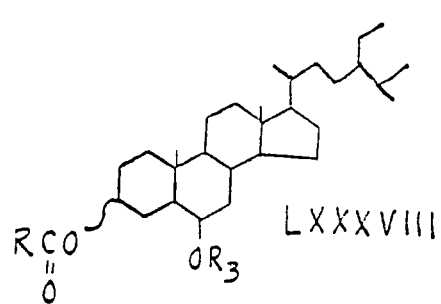 LXXXVIII
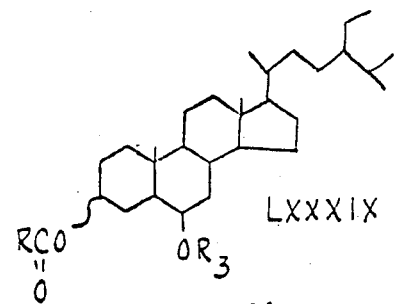 LXXXIX
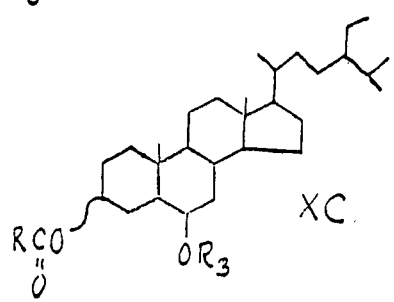 XC
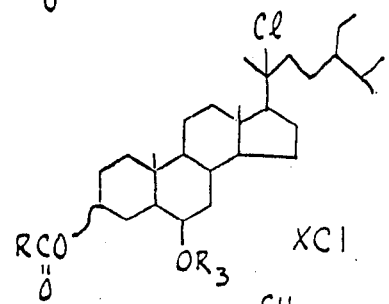 XCI
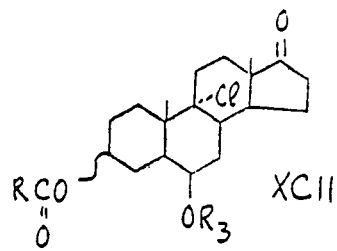 XCII
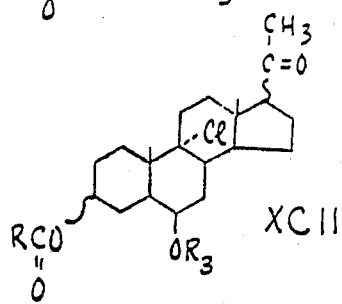 XCIII
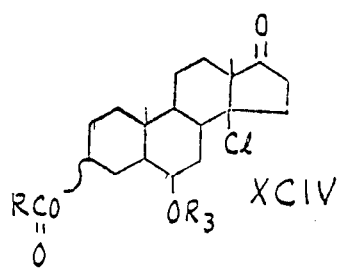 XCIV
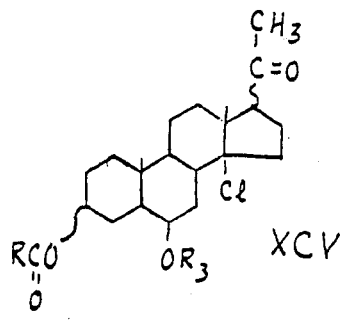 XCV
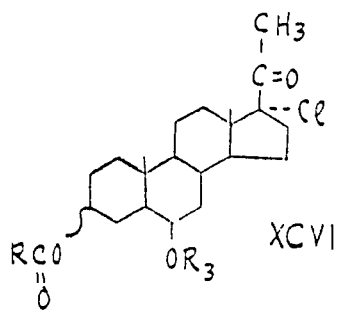 XCVI
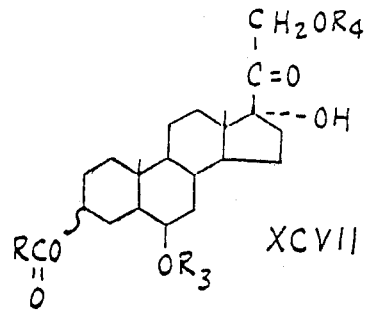 XCVII CHART M CONTINUED (1)
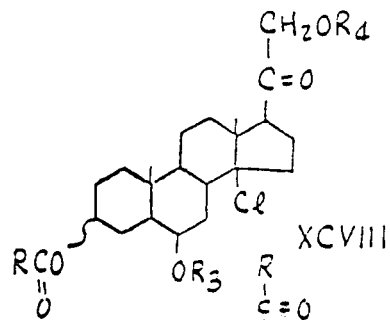 XCVIII
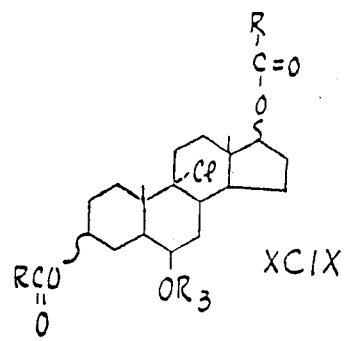 XCIX
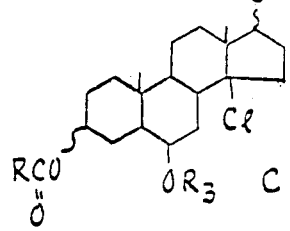 C
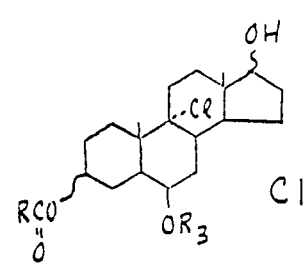 CI
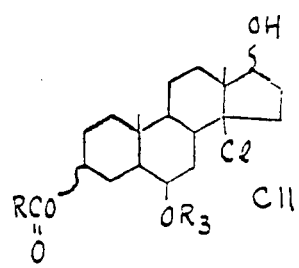 CII
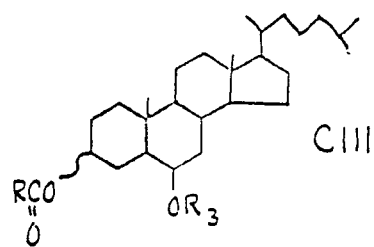 CIII
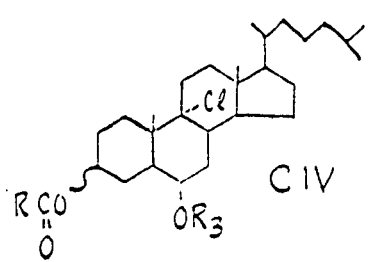 CIV
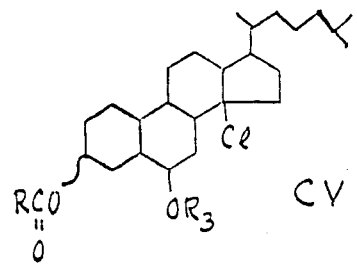 CV
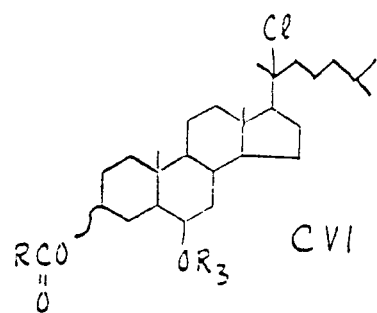 CVI CHART N
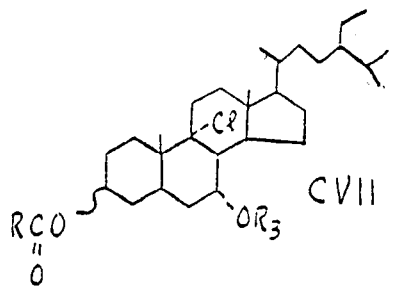 CVII
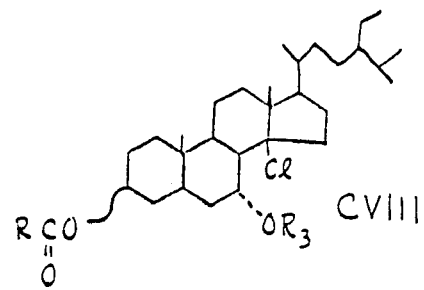 CVIII
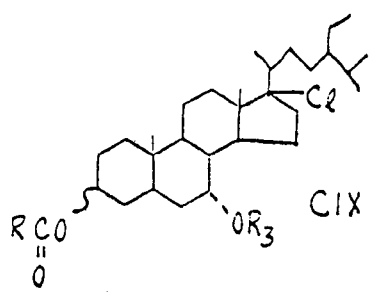 CIX
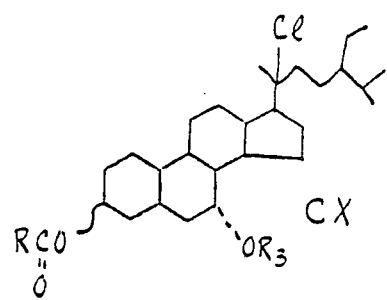 CX
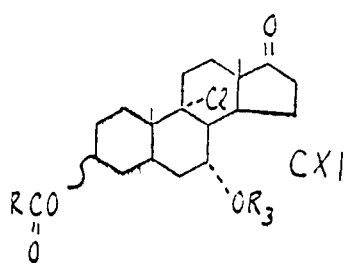 CXI
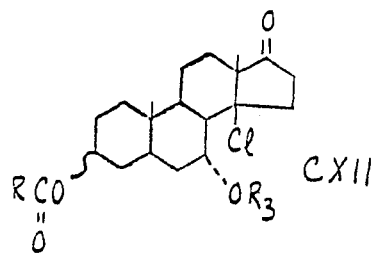 CXII
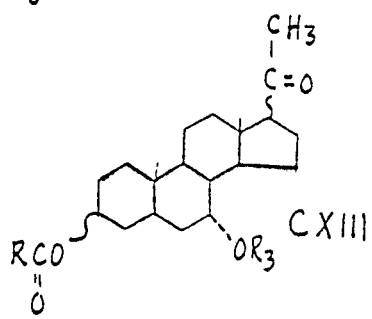 CXIII
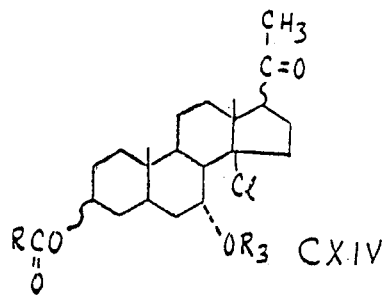 CXIV
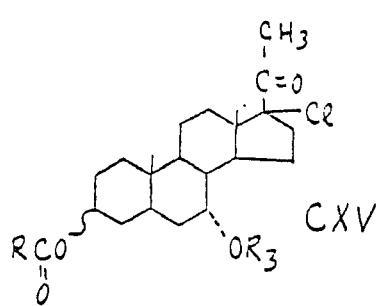 CXV
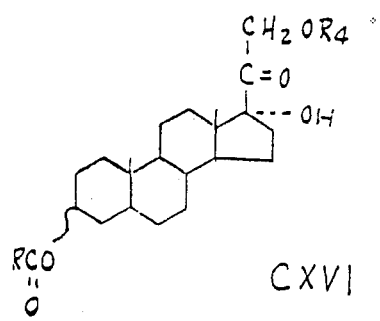 CXVI CHART N CONTINUED (1)
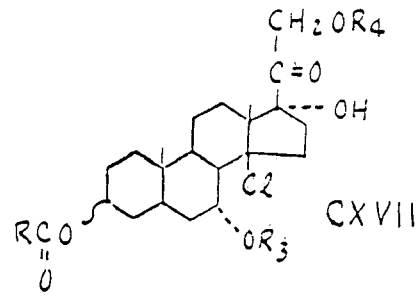 CXVII
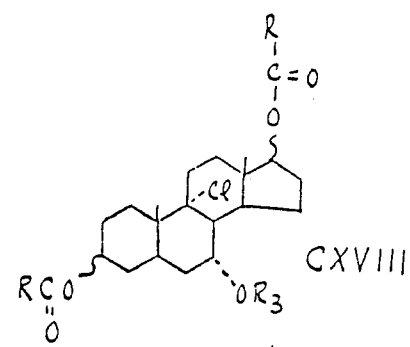 CXVIII
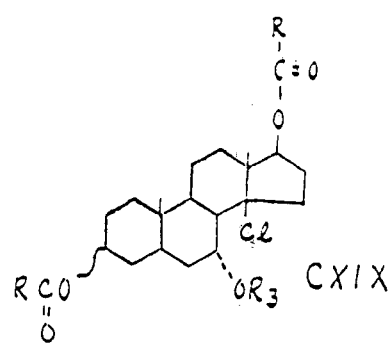 CXIX
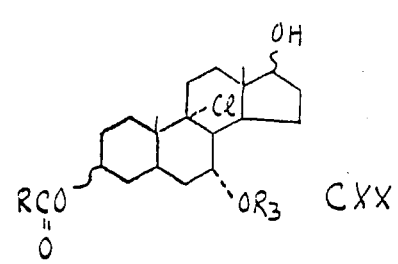 CXX
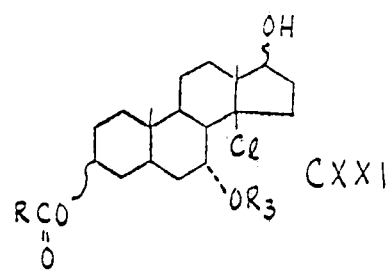 CXXI
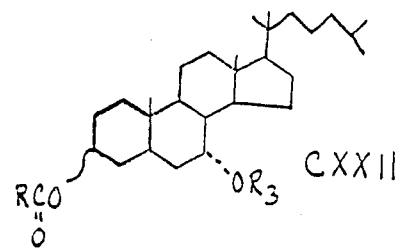 CXXII
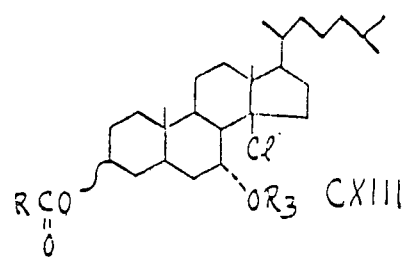 CXIII
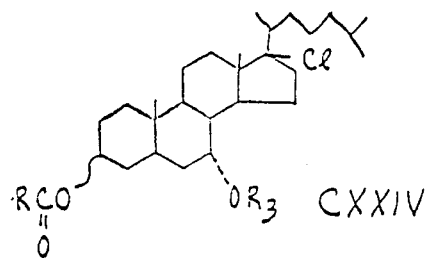 CXXIV

CHART O
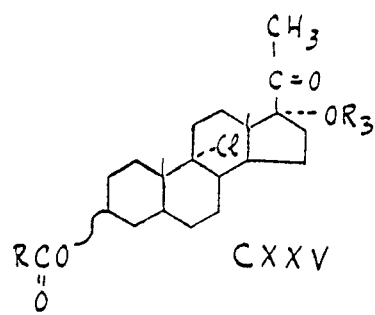
CXXV
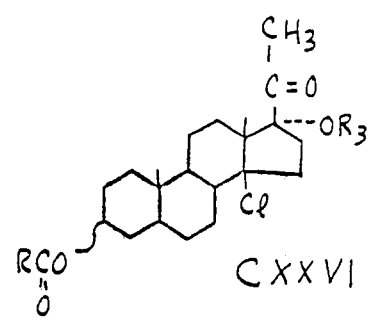
CXXVI
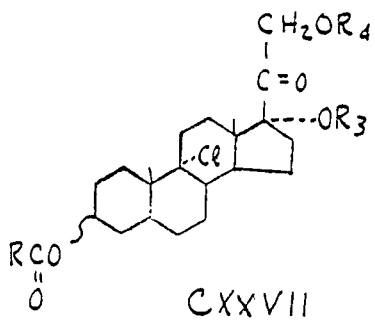
CXXVII
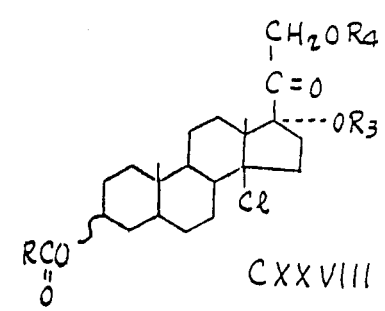
CXXVIII CHART P
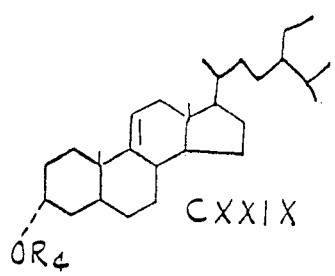 CXXIX
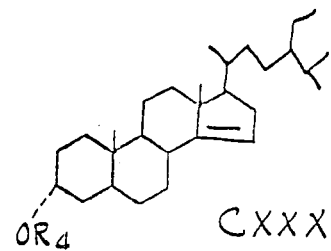 CXXX
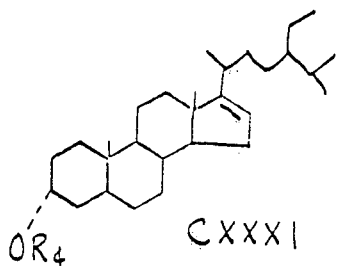 CXXXI
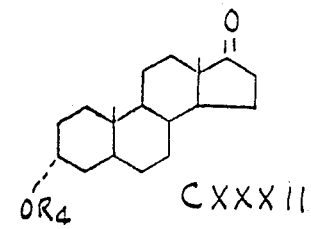 CXXXII
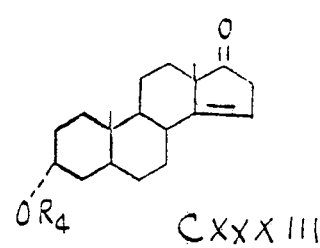 CXXXIII
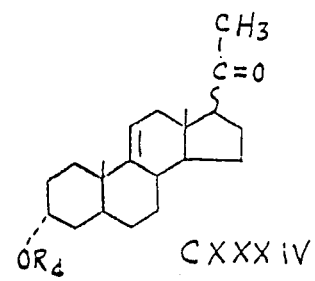 CXXXIV
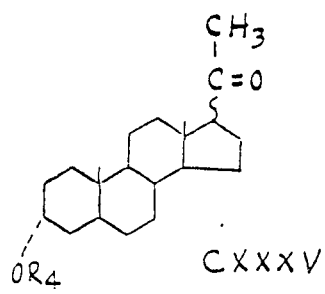 CXXXV CHART P CONTINUED (1)
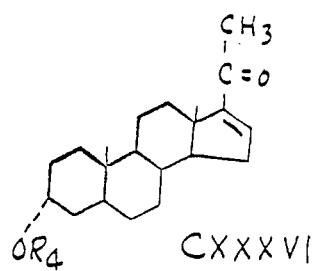 CXXXVI
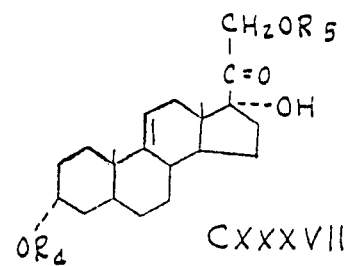 CXXXVII
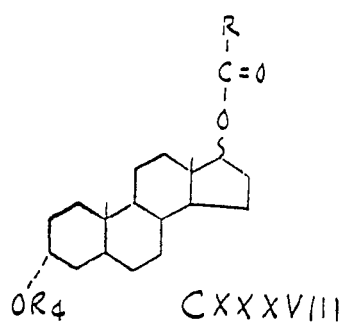 CXXXVIII
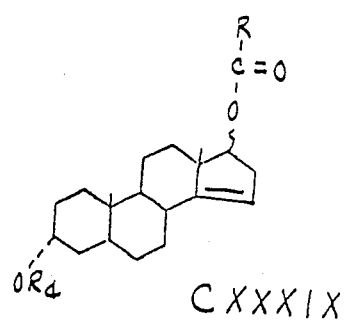 CXXXIX
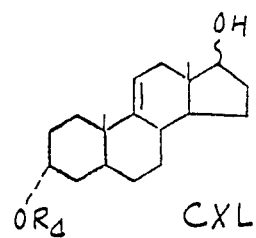 CXL
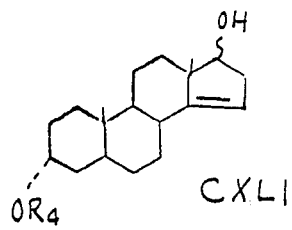 CXLI
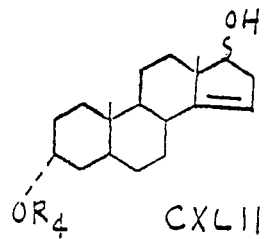 CXLII CHART Q
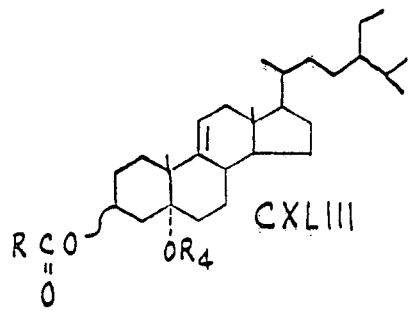 CXLIII
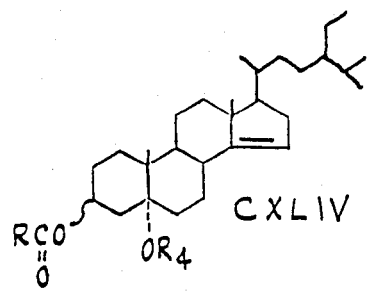 CXLIV
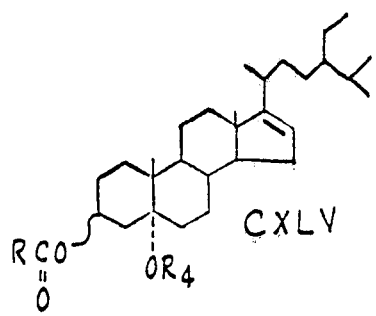 CXLV
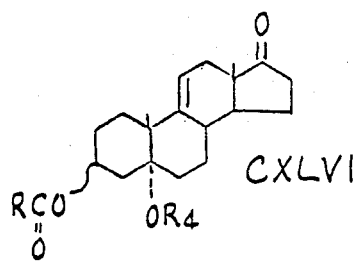 CXLVI
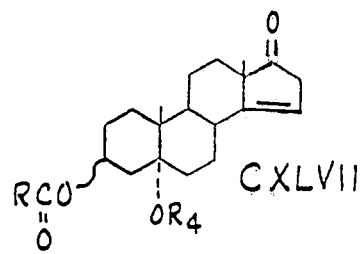 CXLVII
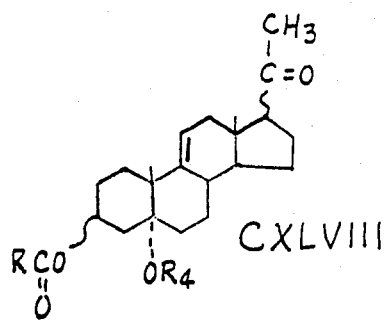 CXLVIII
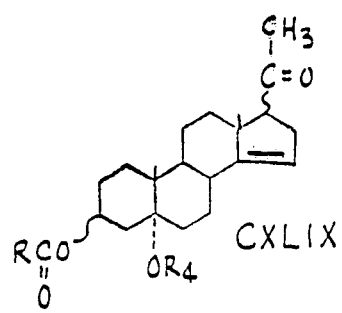 CXLIX
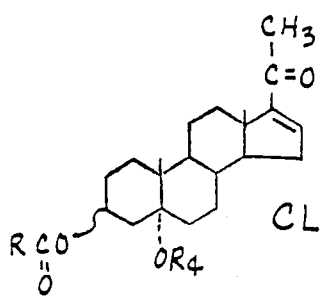 CL
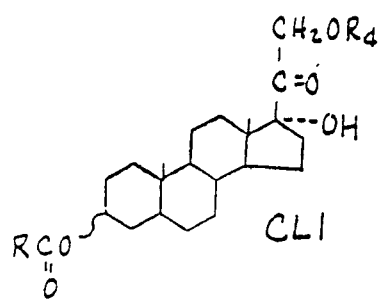 CLI CHART Q CONTINUED (1)
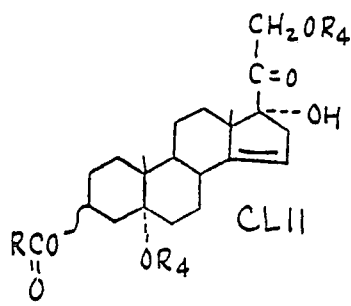 CLII
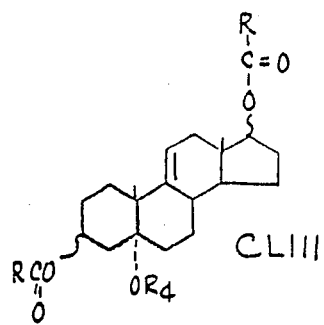 CLIII
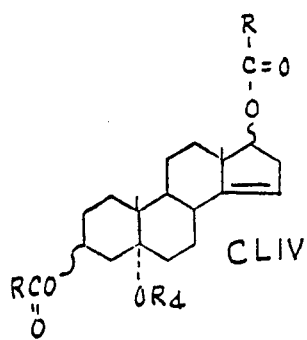 CLIV
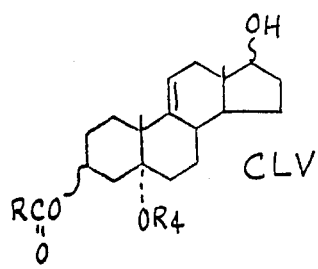 CLV
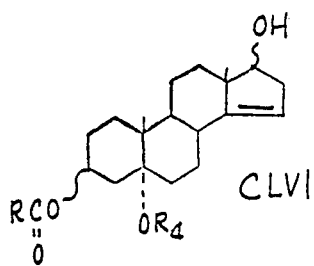 CLVI
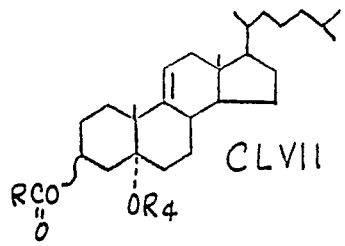 CLVII
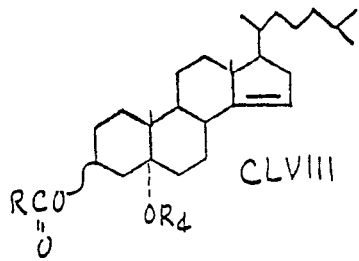 CLVIII
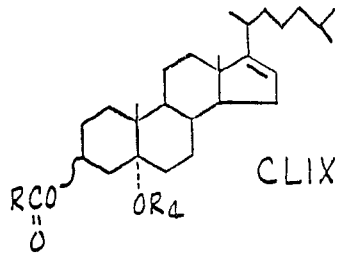 CLIX
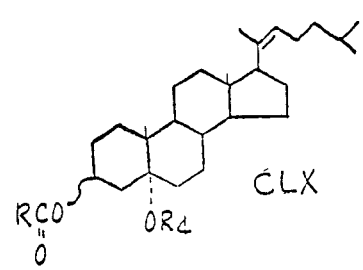 CLX
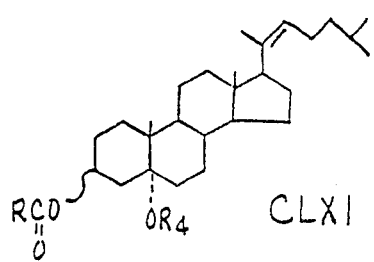 CLXI CHART R
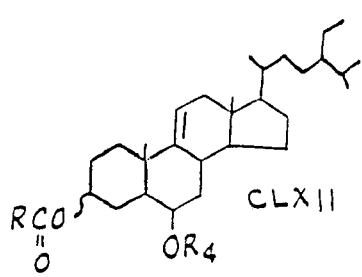
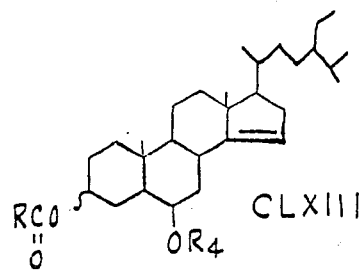
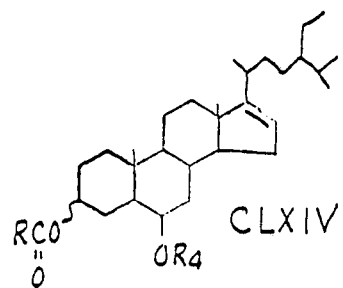
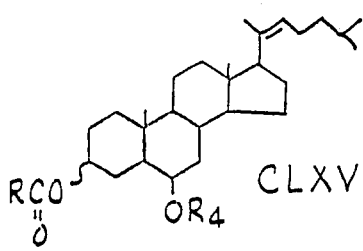
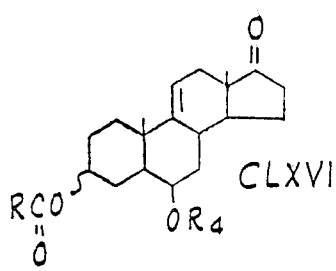
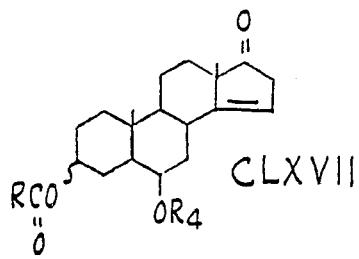
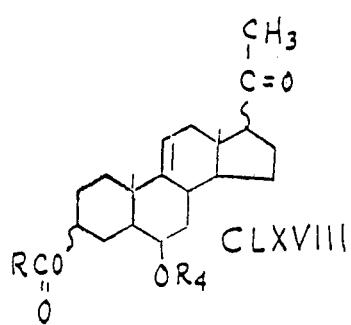
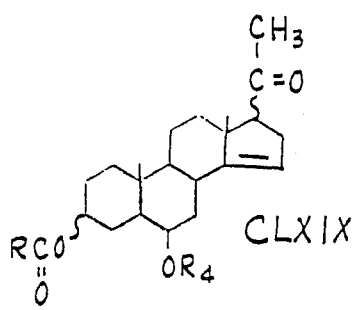
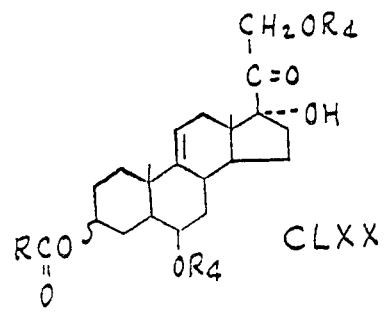

CHART R CONTINUED (1)
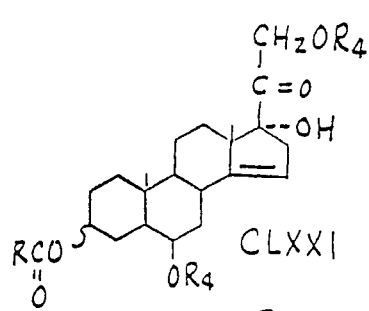
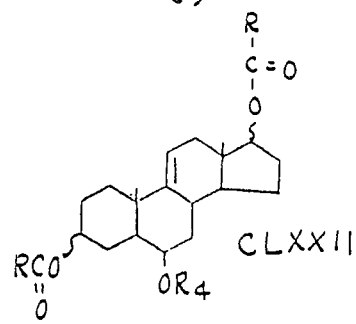
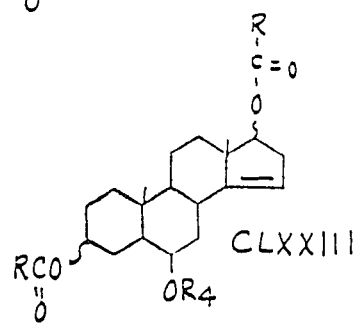
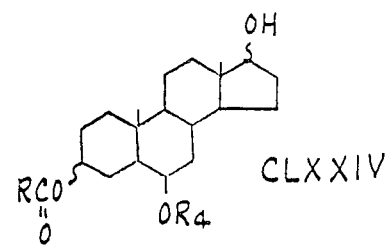
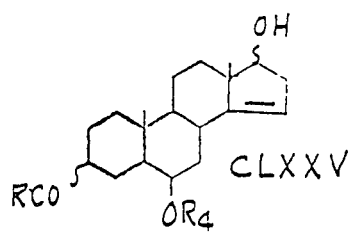
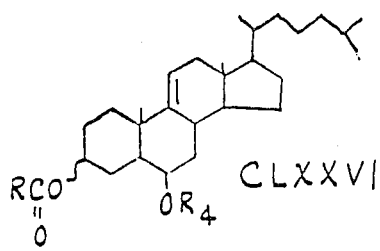
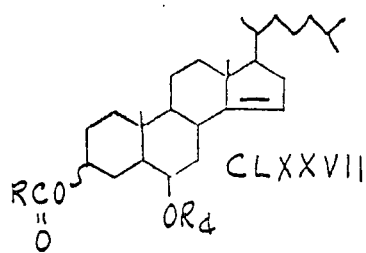
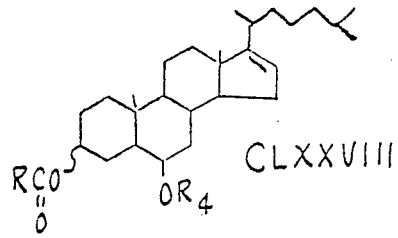
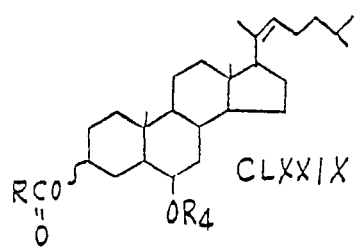

CHART S
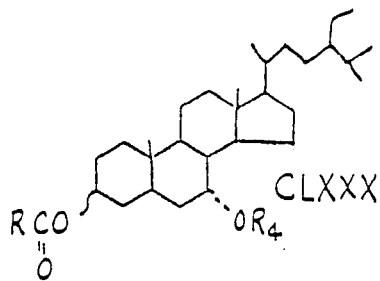 CLXXX
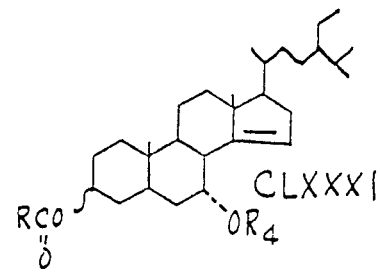 CLXXXI
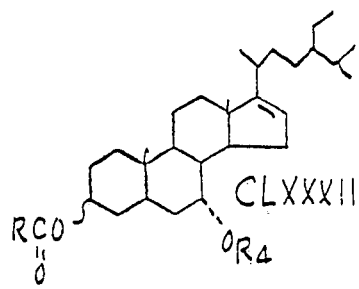 CLXXXII
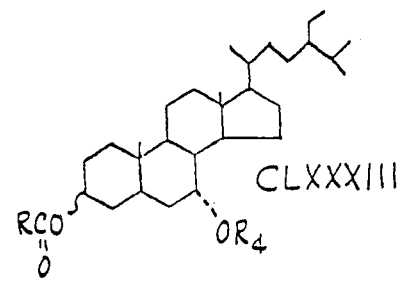 CLXXXIII
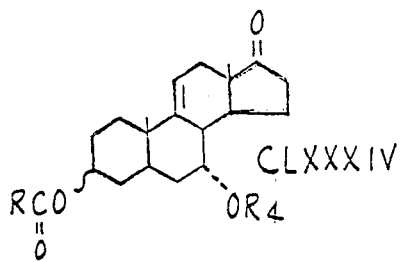 CLXXXIV
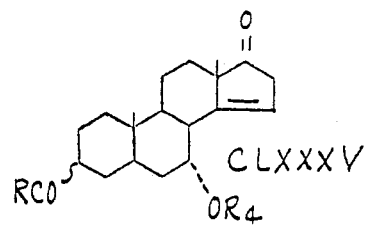 CLXXXV
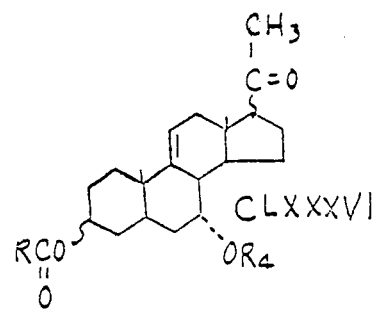 CLXXXVI
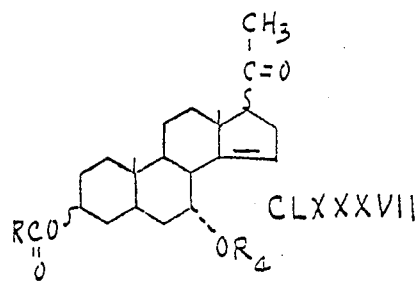 CLXXXVII
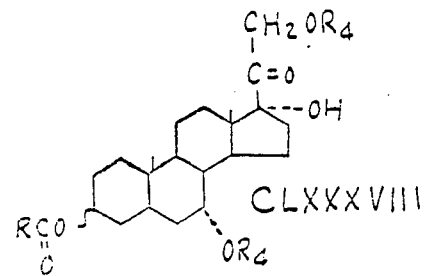 CLXXXVIII CHART S CONTINUED (1)
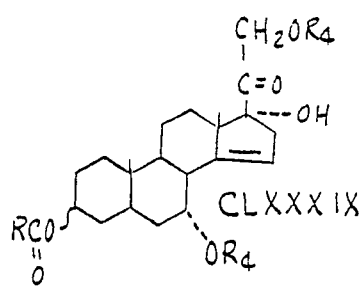
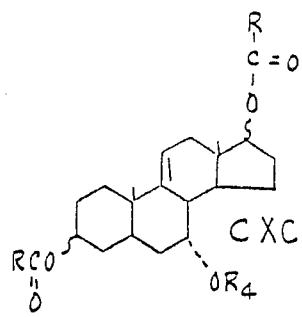
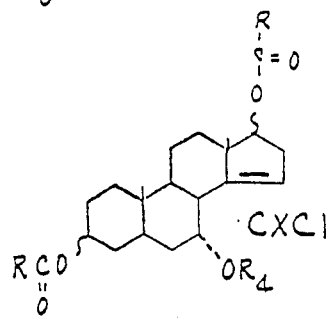
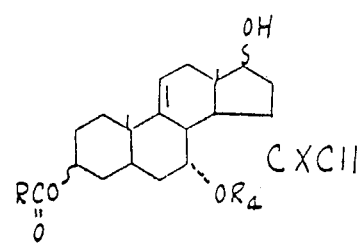
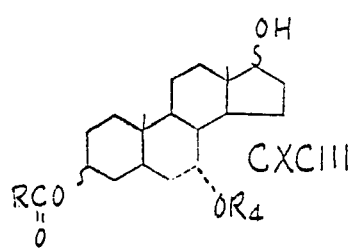
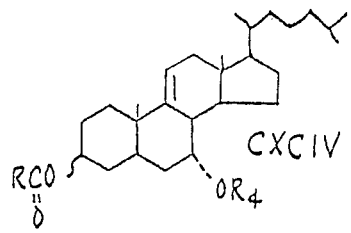
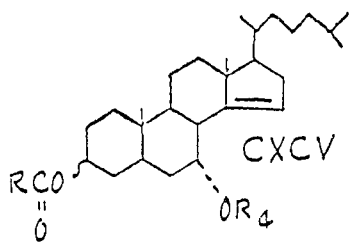
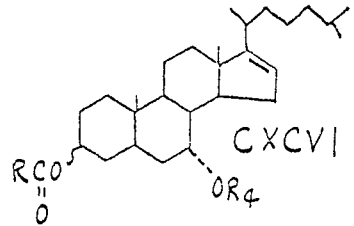
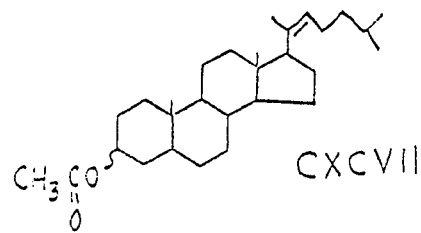

CHART T
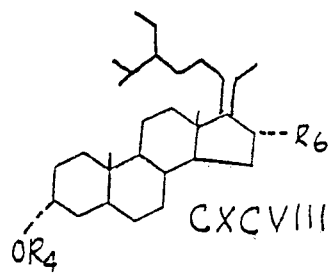 CXCVIII
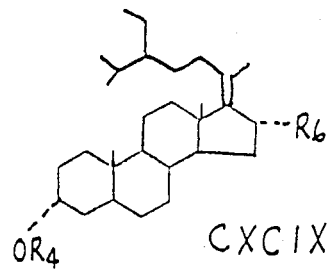 CXCIX
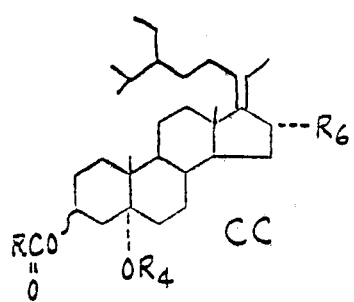 CC
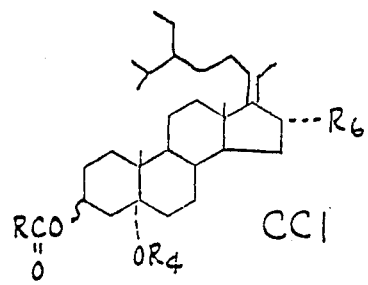 CCI
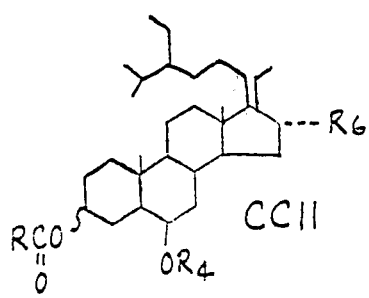 CCII
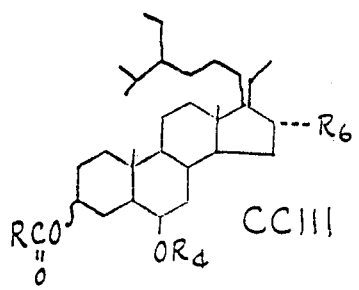 CCIII
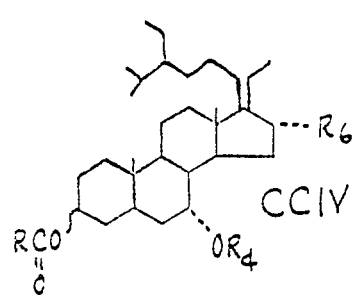 CCIV
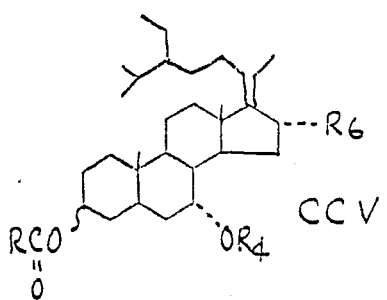 CCV CHART U
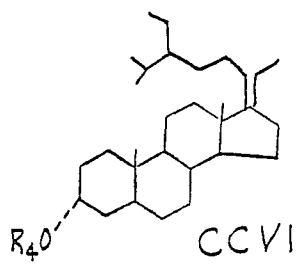
CCVI
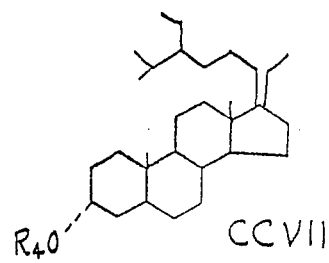
CCVII
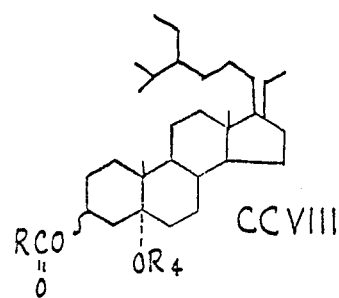
CCVIII
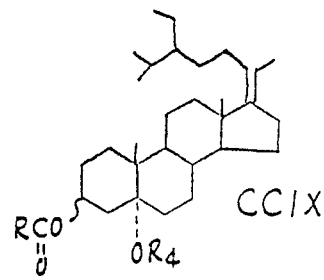
CCIX
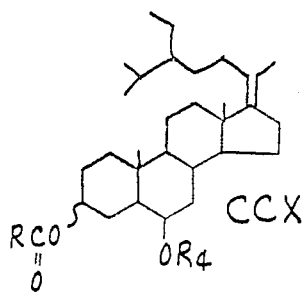
CCX
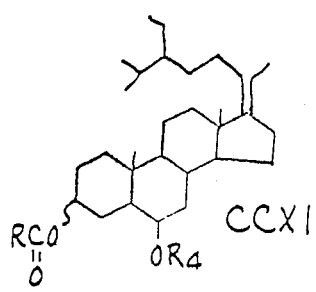
CCXI
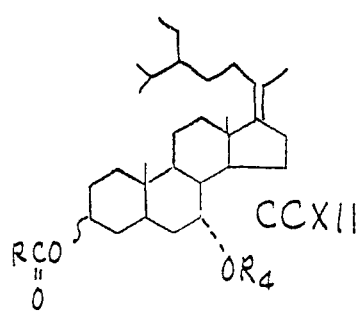
CCXII
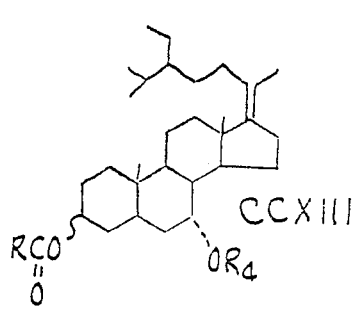
CCXIII CHART V
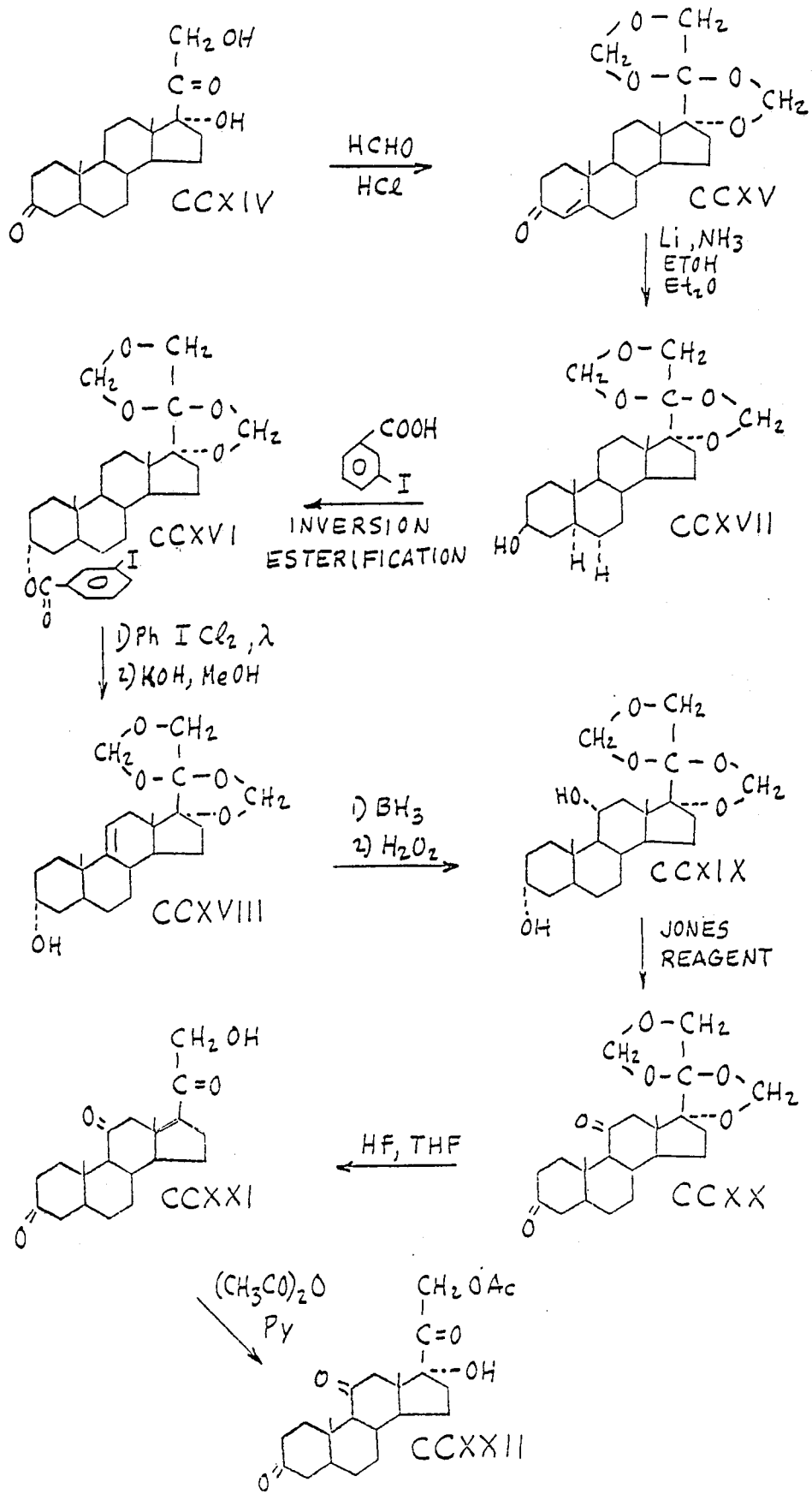

CHART W
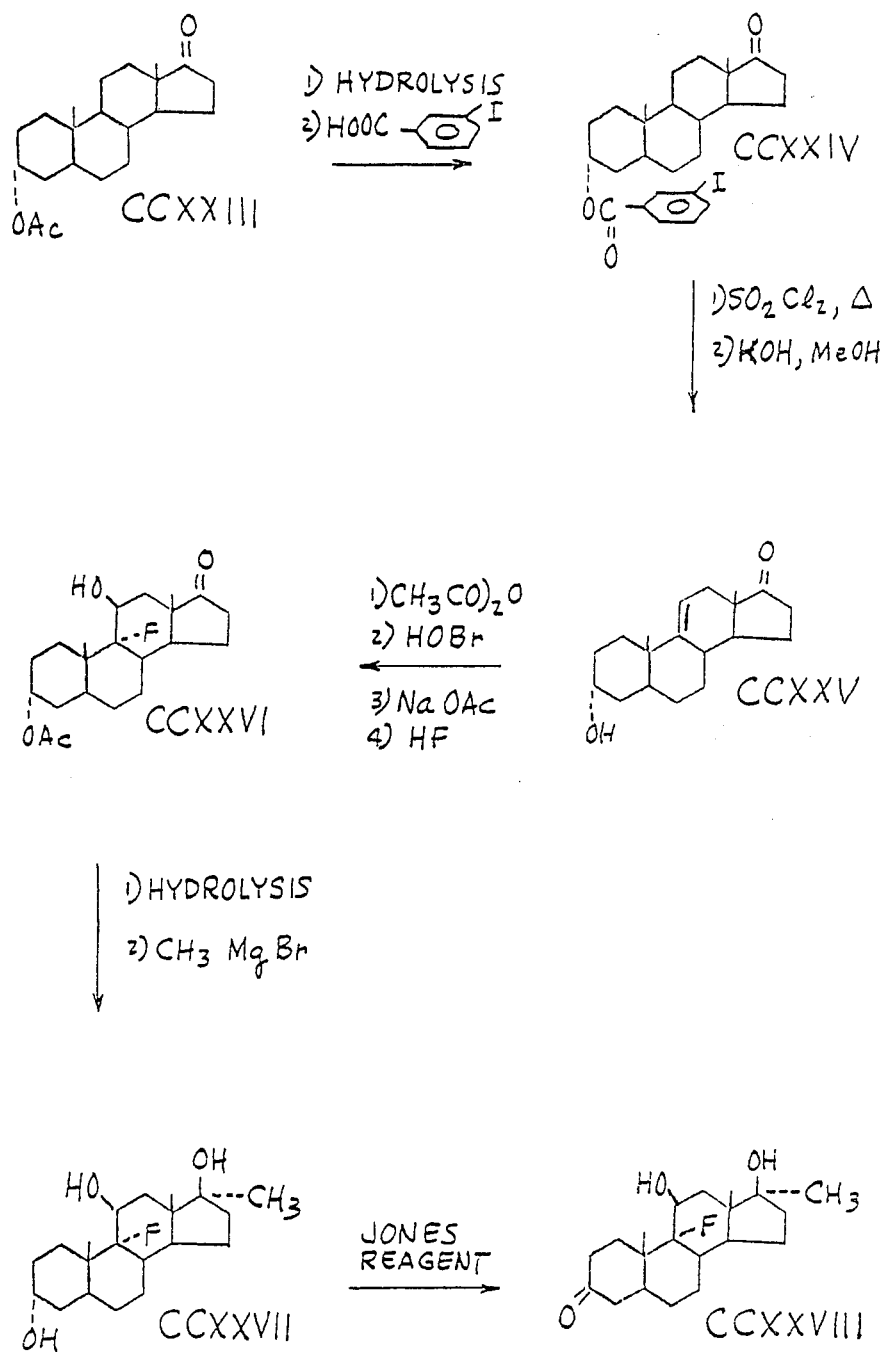

STEROID CONVERSION METHOD AND PRODUCTS PRODUCED THEREBY

The invention described herein was made in the course of work under a grant or award from the Department of Health, Education and Welfare.

This is a continuation of application Ser. No. 786,060, filed Apr. 8, 1977, which is, in turn, a continuation of application Ser. No. 621,163, filed Oct. 9, 1975, both now abandoned.

BACKGROUND OF THE INVENTION

Steroids, particularly 5α-steroids and their 4,5 and 6,7 dehydro analogs, are a well known class of chemical compounds, many members of which are well known for their physiological activity. Steroids with a keto group at the 3-position are especially useful. In the androstane series, 5α-steroids are utilized as anabolic agents and fertility control drugs and for the preparation of these useful compounds. Certain steroids in the pregnane series are particularly effective as anti-inflammatory agents and as cardenolides. Representative steroids in the cholestane series including cholesterol and sitosterols, particularly β-sitosterol, are naturally occurring, and are candidates as starting materials for the commercial preparation of therapeutically useful steroids.

Steroids with a wide variety of substituents on the molecule have proved to be useful for therapeutic purposes. For example, in the pregnane series, 11β-hydroxyl, 6α-fluoro and 6α-chloro substituted compounds having a 9α-fluoro substituent are described as having corticoid activity, and in some cases diuretic activity [see JACS 81, 3156 (1959); JACS 82,3399 (1960); JACS 80, 6464 (1958); U.S. Pat. No. 2,864,836 and U.S. Pat. No. 2,838,547]. In the androstane series, 11β-hydroxyl substituted compounds are described as having antiandrogenic and gonadotropic activity (See U.S. Pat. Nos. 2,731,479 and 2,702,811). Those skilled in this art will be well aware of other variations of the basic steroid nucleus which can be utilized to provide useful compounds.

Many synthetic procedures are available for the production of useful steroids from naturally occurring steroids. Diosgenin is an important source of steroids of the pregnane series such as prednisolone and its numerous derivatives. Because of their ready availability from plant sources, sitosterols, particularly β-sitosterol, have been the subject of many studies to adapt them as commercially useful starting materials for 5α-steroids of the pregnane and androstane series. These studies have not met with significant success. The principal reasons have been the difficulty in removing the side chain, except in low yield, and the difficulty in introducing functional groups into a molecule which is devoid of such groups, except for the 3β-hydroxyl group and the double bond at the 5,6 position.

The available methods for removing the side chain are by either chemical or microbiological oxidation. The yields from each of these procedures are undesirably low. Moreover, the capital investment required to construct, operate and maintain a plant for a microbiological oxidation is very significant.

For these and other reasons well known to those skilled in the art, there have been continuing efforts to devise novel methods for the production of useful steroids

THE INVENTION

A method has now been discovered for the facile, selective removal of tertiary hydrogen atoms on steroid nuclei and side chains. In the method, steroid esters esterified with ester groups to be hereinafter more fully defined are chlorinated under free radical generating conditions to replace the selected hydrogen with a chlorine atom. The chlorinated steroid is thereafter dehydrochlorinated.

The esterifying agents utilized in the practice of this invention are iodoaryl substituted acids, acid anhydrides or acid chlorides which by suitable reaction can form esters of hydroxy steroids in which the iodine atoms is appropriately placed so that when it becomes covalently bonded with a chlorine atom, the chlorine atom is capable of approaching into reactive proximity with the hydrogen atom to be removed. Normally, the chlorine atom will be sufficiently close to the replaceable hydrogen atom if the internuclear distance between the chlorine and hydrogen atoms is from 1.3 to 2 angstroms. The distance between the atoms can be determined by physical measurements. However, the most convenient procedure for determining the suitability of a particular ester group for directing a chlorine atom to a predetermined position on the steroid nucleus is to construct a scale model of the steroid ester and rotate the ester group. It can be readily ascertained by visual observation, whether or not the steroid ester will be suitable for the practice of this invention.

While the process of the invention can be generally applied to the removal of tertiary hydrogen atoms from the nucleus and side chains, it is especially useful for the removal of tertiary hydrogen atoms at the 9, 14, 17 or 20-positions of 3, 5, 6, 7 or 17-hydroxyl-5α-steroids of the cholestane, androstane and pregnane series. It is especially preferred for the stigmastane series, since compounds of this series are more readily available from natural sources.

For convenience in the further description of this invention reference may be had to Chart A which illustrates the process for the preparation of $\Delta^{9,11}$-pregnane-3α-ol-20-one 3-acetate from 5α-pregnane-3α-ol-20-one. Of course, it is not essential to prepare the acetate, but it is often more convenient to separate and purify an ester rather than an alcohol, especially by chromatographic techniques, since the ester is less polar than the alcohol.

In Chart A and other charts of this application illustrating reaction sequences, only the principal products are shown.

The initial ester utilized in the synthetic sequence illustrated in Chart A is the m-iodobenzoate of the starting steroid. This product is conveniently prepared by reaction between the pregnane and m-iodobenzoic acid or m-iodobenzoyl chloride in accordance with procedures well known in the art.

A feature of this invention is that chlorination takes place directly without preparing an intermediate aryl iodine dichloride ester, as was previously believed to be a necessity [See JACS 96, 1973 (1974)]. A particular advantage of the process is that an excess of chlorinating agent can be used without excessive interference by undesirable side reactions, thus making it possible to achieve substantially complete reaction of the steroid starting material.

The selection of the proper steroid ester is a most important aspect of this invention. Its importance can be readily understood from a consideration of what is presently believed to be the reaction mechanism by which a hydrogen is abstracted from a specific position on the steroid nucleus and replaced with a chlorine atom. The mechanism as applied to the preparation of 9α-chloro-androstane-3α-ol-20-one 3-m-iodobenzoate is illustrated in Chart B.

In accordance with the reaction sequence of Chart B, phenyliododichloride is converted to a free radical form with the production of a chlorine free radical. The chlorine atom still bonded to the iodobenzene transfers to become covalently attached to the steroid ester, with the production of another intermediate free radical which may be considered to be a α-complex with the attached aryl iodide.

The formation of the complex brings the covalently bound chlorine atom into reactive proximity with the 9α-hydrogen. This atom is removed with the formation of a free radical at the 9-position and hydrogen chloride. The free radical at the 9-position is neutralized with the formation of a 9α-chloro steroid, regeneration of the phenyliodochloride free radical and continuation of the reaction.

The important point, therefore, in the selection of the esterifying reagent is that it be an iodoaryl substituted group with molecular dimensions such that the chlorine which becomes covalently bonded to the iodine atom is so positioned that it can form hydrogen chloride with the hydrogen atom to be replaced.

Chart B illustrates the conversion of 5α-androstane-3α-ol-17-one (androsterone) to the corresponding 9α-chloro compound. Compound VIII can be isolated, or converted to the corresponding $\Delta^{9,11}$-3α-ol or its acetate in a manner completely analogous to the procedure illustrated in Chart A.

Charts A and B illustrate the abstraction of a 9α-hydrogen atom from a 3α-hydroxy steroid by an initial formation of a m-iodobenzoate. Other esterifying agents are available for the selective removal of other tertiary hydrogen atoms by the formation of esters at the 3α or other positions on the steroid. In general, these are iodoaryl substituted esterifying agents. Iodophenyl substituted reagents are preferred since they are generally more readily available. These include esterifying agents in which the iodophenyl group (or iodoaryl group) is substituted on the carbon atom of an aliphatic chain, as in m-iodophenylacetate or p-iodophenylpropionate. The aryl group, however, may generally contain up to twelve carbon atoms and may, for example, be an iodine substituted fused ring as in naphthyl, or joined phenyl rings as in biphenyl.

While the steroid esters have thus far been described as esters of hydroxy steroids, it will be apparent that the esters need not be prepared from hydroxyl substituted steroids. They may, in fact, be prepared from epoxy steroids by procedures known to those skilled in the art.

The following table illustrates some typical applications of this invention for the removal of specified hydrogen atoms utilizing selected esterifying agents at defined positions:

| Esterified Position | Hydrogen to be Removed | Esterifying Group |
|---|---|---|
| 3α | 9 | m-iodobenzoate |
| 3α | 14 | p-iodophenylacetate |
| 3α | 14 | m-iodophenylacetate |
| 3α | 14 | m-iodophenylpropionate |
| 3α | 17 | 4'-iodo-3-biphenylcarboxylate |
| 5α | 14 | m-iodobenzoate |
| 5α | 17 | p-iodophenylacetate |
| 5α | 17 | m-iodophenylpropionate |
| 6α | 20 | p-iodophenylacetate |
| 7α | 17 | m-iodobenzoate |
| 17α | 9 | m-iodobenzoate |

For convenience, the values assigned to R, $R_1$, $R_3$, $R_4$ and $R_5$ in the appended charts are summarized at this point.

R—alkyl group containing up to five carbon atoms
$R_1$—iodoaryl substituted carboxylic ester group
$R_3$—iodoaryl substituted carboxylic ester group or hydrogen
$R_4$—hydrogen or acyl containing up to five carbon atoms
$R_5$—hydrogen or acyl containing up to five carbon atoms Charts A and B illustrate the use of molecular chlorine and phenyliododichloride as chlorinating agents. Sulfuryl chloride is another of the presently preferred chlorinating agents. Each of these is capable under free radical inducing conditions of generating a σ-complex of a chlorine with an aryl iodide attached to a steroid nucleus.

In its most useful aspects, the process of this invention comprises a method for the selective removal of a tertiary hydrogen atom at the 9, 14, 17 or 20 position of a 3, 5, 6, 7 or 17-hydroxyl-5α-steroid of the cholestane, androstane, or pregnane series which comprises producing an ester of the said hydroxyl steroid with an esterifying agent carrying an iodoaryl group containing up to 12 aromatic carbon atoms and selected so that a chlorine atom covalently bonded to the iodine atom of the iodoaryl group is capable of approaching sufficiently close to the hydrogen atom to be removed so that the internuclear distance between the said chlorine and hydrogen atoms is from 1.3 to 2 angstroms, and thereafter;

(1) reacting the ester under free radical generating conditions with a molar excess of a halogenating agent selected from the group consisting of molecular chlorine, phenyliododichloride and sulfuryl chloride to replace the selected hydrogen with a chlorine atom, and (2) dehydrochlorinating the resulting product.

Those skilled in the art will recognize that the first step in the reaction sequence of this invention is the replacement of the selected tertiary hydrogen with a chlorine atom. The chlorine substituted steroid can be isolated if desired, or converted without isolation to the dehydrohalogenated compound. Direct formation of the double bond, that is, formation of the dehydro compound without isolation of the chlorinated compound is usually preferred since it is generally desired to obtain the double bond in the most convenient manner. The double bond is, as will be recognized, a very useful site for further reaction to introduce other functional groups into the steroid nucleus.

For example, valuable 9α-fluoro steroids can be prepared from $\Delta^{9,11}$-steroids by the following sequence of reactions:

1. React $\Delta^{9,11}$-steroid in peroxide free dioxane with up to about a 50% molar excess of hypobromous acid at a temperature of from 20° C. to 40° C. for from .1 to 4 hours to produce 9α-bromo-11β-hydroxyl steroid,
2. React resulting compound with up to a 200% molar excess of sodium acetate in methanol at from 20° C. to 75° C. for from 1 to 20 hours to produce a 9,11-epoxide,
3. React epoxide with a molar excess of anhydrous hydrogen fluoride in a 1:1 mixture of chloroform and tetrahydrofuran for from to to 6 hours at from −30° C. to 0° C.

It will be recognized, of course, that many useful steroids, especially in the pregnane and androstane series are characterized as $\Delta^4$ or $\Delta^5$ steroids because of the double bond at the 4 or 5 position. These compounds are not, strictly speaking, 5α-steroids. However, since they are normally derived from 5α-steroids they should, for convenience in this disclosure, be considered as included within the scope of the term 5α-steroids.

Typical compounds to which the process of this invention is applicable includes those, the partial structures of which are shown in Chart C. The structures are partial in that no esterified hydroxyl groups are shown. It will be understood, of course, that these groups may be present on the steroid nucleus as indicated above. The starting compounds for the preparation of the esters of the hydroxylated compounds are all known or can be prepared from known compounds by known methods.

The utility of compounds XII and XIV illustrate an aspect of this invention which is very valuable, that is, that other functional groups may be present in the molecule without adverse effect. Thus, for example, keto groups, other hydroxyl groups, double bonds, alkyl groups, halogen atoms and the like may be present on the esterified compound without interfering with the basic process. In some cases it may be desirable to block other functional groups with readily removable blocking groups to prevent interference with the desired reaction. For example, 17, 21-diols may be protected as acetonides before esterification of a 3-hydroxyl steroid with an iodoaryl substituted esterifying agent.

Some care must be exercised, however, with the selection of reagents in the presence of other functional groups. If more than one hydroxyl group is present, all except the group to be esterified with the iodoaryl substituted esterifying agent should be blocked. If a double bond is present in an aliphatic side chain as in 24-dehydrocholestanol, it is best not to utilize molecular chlorine as the halogenating agent. Normally, the esterified hydroxyl group and the hydrogen to be removed will be on the same side of the steroid molecule so that the chlorine atom and the hydrogen to be removed can approach to the internuclear distance required for reaction. A bulky substituent which is otherwise inert to the reagents employed may, if in the proper position, sterically interfere with the approach of the chlorine atom to the hydrogen atom.

For any of a wide variety of reasons, it may be preferred to replace a specific hydrogen with an esterifying group attached at one position rather than another. These may include, for example, the relative cost of available esterifying agents, the ease with which alternate starting compounds may be obtained, the presence of sterically interfering groups, or the relative difficulty in isolating the products prepared. For any of these reasons it may be sometimes desirable, for example, to remove a hydrogen from the 14-position with an iodoaryl ester group at the 3-position rather than the 5-position.

An especially valuable utility for the process of this invention is the production of compounds of the androstane series from those of the cholestane series. The production of androsterone from β-sitosterol is particularly valuable since this starting material is readily available from a wide variety of plant sources. One synthetic procedure for this conversion in accordance with the process of the invention is illustrated in Chart D. The process is similarly applicable to ergosterol.

Although specific reagents are indicated for each reaction step in Chart D, it will be understood that for several of the individual reactions a wide variety of other reactants may be suitable.

The reduction of the double bond at the 5,6-position may be effected with any of a number of known reducing agents.

Inversion esterification of Compound XVIII with 4′-iodo-3-biphenylcarboxylic acid in the presence of triphenylphosphine and diethyl azodicarboxylate may be effected according to the procedure of Bose et al., Tetrahedron Letters, 1619 (1973).

Inversion of the hydroxyl group at the 3-position is carried out since the original hydroxyl group at the 3-position and the 16-hydrogen are on opposite sides of the molecule. With many hydroxyl starting compounds used in the process of this invention, the hydroxyl group will not need to be inverted. The inversion esterification procedure is very convenient since it accomplishes two transformations in one reaction. However, an hydroxyl group may be inverted by any of a number of known procedures prior to esterification.

A very significant number of new compounds are prepared utilizing the process of this invention. Many of them, Compound XIX for example, are valuable intermediates for the preparation of useful steroids, and are specifically included within the scope of this invention. Chart E shows the generic formulas for some of the novel compounds.

In Chart E, $R_1$ is an iodoaryl substituted carboxylic ester group in which the iodoaryl moiety contains up to 12 aromatic carbon atoms, and a chlorine atom covalently bound to the iodine is capable, upon rotation of the ester group, of approaching a tertiary hydrogen atom on the steroid so that at the distance of closest approach, the internuclear distance between the chlorine atom and the tertiary hydrogen atom is from 1.3 to 2 angstroms; and R is as defined above.

It will be understood that while Chart E shows only 3-iodoaryl substituted esters, that analogous compounds in which hydroxyl groups at the 5, 6, 7 or 17-positions are similarly esterified are also novel.

Chart F shows novel 5-hydroxyl steroids within the purview of the invention. Chart G illustrates 6-hydroxyl steroids. Chart H is directed to 7-hydroxyl steroids, and Chart J shows 17-hydroxyl steroids. In the charts, R and $R_1$ have the same meaning as above.

In Charts E through J, the only compounds specifically illustrated with double bonds are Compounds LVI and LVII. These are illustrated because of their importance as intermediates. It will be appreciated, however, that the formulas of Charts E through J illustrate classes of compounds which may contain double bonds, especially at the 4,5 and 5,6 positions.

Starting compounds for the preparation of the novel intermediates generally illustrated in Charts E through J are known or can be prepared from available materials by known methods. In all of the compounds illustrated, other reaction inert substituents may be present on the molecule, including reaction insert substituents which are used to block other reactive groups and may be removed by known procedures when desired. These include, for example, methylenedioxy groups and others such as acetonides, cyclic carbonates, ortho esters, carboxylic nitrate esters, tetrahydropyranyl ethers, trityl ethers, and the like.

The ester with the appropriate aryliodo substituted ester group in place is next chlorinated with molecular chlorine, sulfuryl chloride or phenyliododichloride under free radical generating conditions.

Typically, for reaction with molecular chlorine the steroid to be chlorinated is taken up in a reaction inert organic solvent, preferably polar, and chlorine is added. The reaction temperature is not critical, although obviously it is desirable to keep the temperatures sufficiently low so that the chlorine is not driven from solution and the reactants do not decompose. Normally a temperature of from 0° C. to 70° C. will be sufficient.

Useful solvents which may be mentioned by way of example include aromatic and aliphatic solvents containing up to six carbon atoms. The preferred solvents are polar solvents such as substituted hydrocarbons, particularly halo or cyano substituted hydrocarbons, especially carbon tetrachloride, chloroform, methylene chloride, chlorobenzene or acetonitrile. However, unsubstituted solvents such as benzene or cyclohexane may be used, although they are not preferred.

While some reaction will take place in the presence of even small amounts of chlorine, it is advisable to assure as complete reaction as possible of the more expensive steroid ester to use at least a molar equivalent of chlorine. It is preferred to use from 1.5 to 2.5 molar equivalents of chlorine per mol of steroid.

Free radicals may be generated by any of the usual processes. For example, the solutions may be irradiated with a sunlamp or a tungsten lamp. Alternatively, the reaction may be initiated without irradiation by the addition of redox metal free radical producers including cuprous, ferrous or titanous salts. In a typical example 0.1 equivalent of cuprous acetate may be employed.

Free radicals may also be generated with peroxide or azo compounds such as benzoyl peroxide, diacetyl peroxide, di-t-butyl peroxide, azobisisobutyronitrile or other such compounds at a concentration of 5 to 20 mol percent. The free radical generator is decomposed by heating.

The course of the reaction may be followed by nuclear magnetic resonance, by thin layer chromatography, or other standard analytical procedure. Commonly, the reaction is completed in from 10 to 120 minutes.

When sulfuryl chloride is used as the source of free radicals, the conditions and reagents employed are generally similar to those used with chlorine. However, direct irradiation of the solution is normally not useful except with ultraviolet light.

With phenyliodochloride, free radicals can be produced under the same conditions, or utilizing the same reagents as with chlorine.

Halogenation may be accompanied with inversion. It is presently believed that replacement of α-hydrogens at the 14 or 17 positions results in the formation of β-chlorosteroids.

The chloro steroids usually can be isolated by simply evaporating the solvent. It is also possible to isolate them by chromatography, for example, on silica gel.

Particularly valuable novel compounds within the scope of the invention are illustrated in Charts K through O. In these charts, R and $R_1$ have the same meaning as above.

The reaction in which both hydrolysis and dehydrohalogenation take place are illustrated by the conversion of Compound XXI to Compound XXII on Chart D. Alternatively dehydrohalogenation may be carried out without hydrolysis.

Dehydrohalogenation without hydrolysis is achieved by reaction with a weak inorganic or organic base in a reaction inert organic solvent. Polar ethers or ketones containing up to six carbon atoms, such as diethyl ether, tetrahydrofuran, dioxane, acetone, methyl ethyl ketone, and the like may be employed as solvents. Hydrocarbon solvents, particularly aromatic hydrocarbons, may also be employed.

Typically 1 to 3 equivalents of the selected basic reagent will be employed. Suitable reagents include nitrogenous bases such as triethyl amine and pyridine, or alkali metal bases such as sodium acetate, bicarbonate, carbonate or phosphate.

Reaction is normally complete in 0.5 to 6 hours, but the reaction time may vary appreciably. The reaction can be followed by nuclear magnetic resonance, by chromatography or other suitable procedure.

The products are conveniently isolated by washing with water, extraction into a water imiscible organic solvent such as diethyl ether, or methylene chloride, and removal of the solvent. A high degree of purification can be achieved chromatographically using alumina or silica.

Simultaneous hydrolysis and dehydrohalogenation is normally carried out using a strong base, particularly an hydroxide of an alkali metal such as sodium, potassium or lithium. A reaction inert, polar organic solvent, typically a lower alkanol or ether such as ethanol, tetrahydrofuran or dioxane may be employed to dissolve the steroid ester.

Generally 2 to 10 equivalents of alkaline reagent is added and the resulting solution or suspension heated for 0.5 to 5 hours at 25° C. to 100° C.

One convenient method of isolation is to evaporate the solvent and then separate into neutral and acidic portions by extraction between an aqueous alkaline solution such as sodium carbonate and an organic solvent such as ether. The ether layer, which contains the steroid is dried over an anhydrous drying agent such as magnesium sulfate, filtered, and the solvent evaporated to provide the desired product. It may be further purified by chromatography on silica or alumina.

The alkaline solution may be acidified, for example, with a mineral acid such as hydrochloric or sulfuric to permit recovery of the iodoaryl acid for reuse. Recovery may be by filtration or by extraction into an organic solvent.

It is not necessary to directly isolate the hydroxylated steroid. Either the crude or the purified steroid may be acylated by reaction with an acylating agent containing up to six carbon atoms. Acid chlorides and anhydrides such as acyl chloride or acetic anhydride are the preferred acylating agents.

Generally the reaction is carried out in a reaction inert solvent such as pyridine utilizing 1 to 2.5 equivalents of acylating agent at 20° C. to 100° C. for from 0.2 to 4 hours.

Any standard isolation procedures are suitable. The product may be recovered by simple evaporation of the solvent.

Purification may be effected chromatographically on silica or alumina.

General formulas for several of the valuable new compounds specifically included within the scope of this invention are illustrated in Charts P through S.

In Charts P through S, $R_4$ and $R_5$ are hydrogen or acyl, specifically lower acyl containing up to five carbon atoms. Normally it will be acetyl since this is the most convenient. Usually $R_4$ and $R_5$ will be identical, although this is not essential.

The conversion of Compound XXII to Compound XXIII shown on Chart D is the next step in the conversion of sitosterol to androsterone.

The reaction is one in which ane ene-adduct is formed by reaction of the 16,17-unsaturated compound with an enophile. The enophile may be selected from any of a variety of known reactive species. The reactant illustrated is N-phenyltriazolinedione. However, other reagents such as lower alkyl (up to 6 carbon atoms) azodicarboxylic esters, hexafluorothioacetone, or singlet oxygen can also be employed.

With the first mentioned compound, the product is a triazolidinedione. The azodicarboxylic ester forms a 1,2-dicarboalkoxy hydrazine. Oxygen forms hydroperoxide, and the thioacetone forms a hexafluoroisopropylsulfenyl adduct.

It will be seen that in the course of the reaction an ene-adduct forms, and is in general a species derived from the original enophile in which a hydrogen has been added to one atom of the original double bond in the enophile while the other, originally unsaturated atom is now attached to carbon 16 of the steroid.

In forming the ene-adduct with N-phenyltriazolinedione the steroid is dissolved in a reaction inert organic solvent such as a halogenated hydrocarbon solvent containing up to two carbon atoms such as methylene chloride, ethylene dichloride or chloroform. It is best to use at least a molar equivalent of the enophile, and as many as 2.5 equivalents or even more can be used without adverse effect. Any convenient temperature from 20° C. to 100° C. is suitable, and reaction is normally complete in from 2 to 25 hours. Considerable departure from these ranges can be tolerated without loss of yield.

The product may be isolated by simple evaporation of the solvent at reduced pressure. It is, in many cases, sufficiently pure for the next step, but if desired, it may be purified chromatographically with silica, alumina or similar material.

The reaction with azodicarboxylic esters is carried out in a similar manner. However, somewhat higher temperatures and longer times, say for example, 50° C. to 150° C. for 5 to 30 hours, are preferred.

Reaction with oxygen is conducted under irradiation utilizing a photosensitizer such as methylene blue or other such compound while bubbling oxygen through a solution of the steroid in one of the solvents described above. The reaction may be followed with nuclear magnetic resonance or thin layer chromatography. It is normally complete in from 16 to 24 hours.

The reaction with hexafluorotioacetone is conducted in a reaction inert solvent as mentioned above. Reaction normally takes place during a period of from 0.5 to 3 hours at a temperature of from 0° C. to 40° C. while 1 to 1.5 equivalents of enophile is cautiously added.

The next reactions shown on Chart D are the reduction of the ene-adduct followed by oxidation to remove the side chain. The reactions may be reversed so as to initially remove the side chain and then reductively remove the enophile moiety.

The presently preferred reduction procedure is reduction with an alkali or alkaline earth metal in an amine solvent. Lithium in ethyl amine is the preferred reducing agent. However, other mono and polyamines containing up to four carbon atoms such as propyl amine and ethylene diamine may be employed. Calcium, potassium or sodium metal may be utilized in place of the lithium.

The reduction is normally complete in from 0.5 to 6 hours at a temperature of from 0° C. to 50° C. utilizing from 2 to 5 equivalents of metal.

Reaction inert cosolvents such as ethers may be employed. The reduction may also be conducted in reduction stable, hindered alkanols such as tertiary butanol.

Alternatively, reductive removal of the ene-adduct may be performed after double bond oxidative cleavage. In this case methods of reduction for removal of the ene-adduct include reduction with amalgamated magnesium or aluminum, or with a soluble chromous salt such as chromous chloride, or with a metal such as zinc.

These reactions are generally carried out in an oxygenated, polar solvent such as alkanols, ethers or carboxylic acids, suitably containing up to four carbon atoms such as ethanol, acetic or propionic acid, or dioxane. An excess of reducing agent is normally employed, for example, from 2 to 5 equivalents based on the amount of steroid to be reduced. The reaction temperature may be from 20° C. to 100° C., and the reaction is normally complete in from 5 to 6 hours.

The usual methods of isolation for this type of reaction will be utilized. For example, the solvent is evaporated, and the residue extracted between water and a suitable organic solvent such as ether, chloroform or methylene chloride. The organic solvent is dried, filtered and evaporated to leave the desired product as a residue. It may be purified by chromatography over silica, alumina or similar material.

The oxidation step in Chart D is illustrated as ozonolysis. However, those skilled in the art will recognize that other oxidation procedures will also be useful. As stated above, oxidation may be effected before or after reduction.

For oxidation with ozone, the presently preferred procedure is to take up the steroid in one of the solvents mentioned above, or any of the other solvents commonly employed for oxidation, and to pass from 1 to 2.5 equivalents of ozone through the solution at a temperature of from −80° C. to 30° C. for a period of from 0.5 to 3 hours. The product may be isolated by evaporation of solvent and excess ozone. It may be further purified by chromatography with alumina or silica.

The steroid may also be oxidized with a number of other oxidizing agents. Thus, a solution of potassium permanganate in acetone may be used with an acetone solution of the 17,20 olefin, with or without the ene-adduct at carbon 16, in order to produce the 17-one with or without the ene-adduct at 16. In this case, the reaction is performed at a temperature range of from 0° C. to 70° C. with usually only a 10–20% excess of potassium permanganate, sodium permanganate, or similar material.

In addition, the 17,20 double bond can be oxidatively cleaved using catalytic amounts of ruthenium tetraoxide with molar amounts of sodium periodate. This reaction is generally performed in solvent mixtures, comprising in part inert, organic solvents such as carbon tetrachloride, methylene chloride, and the like which are resistant to oxidation together with small amounts of water or other cosolvent such as acetone to help dissolve the inorganic reagents at least partially in the reaction mixture.

These oxidations by inorganic reagents, including both the permanganate oxidation and the periodate procedure, are then followed by normal extraction between water and organic solvents, such as methylene chloride, ether, etc., drying of the organic layer, and removal of the solvent by evaporation to afford the product which may be purified by chromatography on silica, alumina, or similar materials.

Compounds XXIII and its ene-adduct analogs as well as Compounds XXIV and XXV are representative of the novel compounds prepared by the process of this invention. Novel compounds analogous to Compounds XXIII are illustrated on Chart T, and to Compounds XXIV and XXV on Chart U. In Chart V, $R_6$ represents an ene-adduct moiety.

Not all of the compounds or classes of compounds illustrated in the charts are new compounds. Several of them are known compounds whose utility per se or as intermediate for the preparation of other known compounds by known routes is well known and recognized. They are shown merely as an aid in understanding the importance and versatility of this invention for the preparation of a wide variety of useful compounds.

Those compounds believed to be novel, and their equivalents are included within the scope of the claims of this application.

The following non-limiting examples are given by way of illustration only.

EXAMPLE I

Esterification in the Cholestane Series

Meta-Iodobenzoate of 3α-Cholestanol

3α-Cholestanol (4.85 g, 12.5 mmol) and meta-iodobenzoylchloride (3.37 g, 12.7 mmol) are dissolved in 20 ml of dry benzene and 2 ml of pyridine added. The mixture is heated at 80° under $N_2$ for 8 hours. The solvent is removed on a rotary evaporator and the residue diluted with 200 ml of ether. This is washed twice each with 25 ml portions of both 10% hydrochloric acid and sodium bicarbonate. The organic layer is dried (MgSO$_4$) and evaporated and the residue recrystallized from ethanol to afford 6.6 g (84% yield) of colorless crystalline ester: mp 89.5°–90.5°. anal. calcd. for $C_{34}H_{51}O_2I$: C, 66.00; H, 8.31; I, 20.51. Found: C, 66.44; H, 8.17; I, 20.58.

The following compounds are similarly prepared.
m-iodobenzoate of 3α-5,6-dihydrositosterol;
p-iodophenylacetate of 3α-cholestanol; m.p. 93° C. to 97° C.
p-iodophenylacetate of 3α-5,6-dihydrositosterol
m-iodophenylacetate of 3α-cholestanol; m.p. 89° C. to 90° C.
p-iodophenylacetate of 3α-5,6-dihydrositosterol
m-iodophenylproprionate of 3α-cholestanol
m-iodophenylpropionate of 3α-5,6-dihydrositosterol
4'-iodo-3-biphenylcarboxylate of 3α-cholestanol; m.p. 117° C. to 118.3° C.
4'-iodo-3-biphenylcarboxylate of 3α-5,6-dihydrositosterol; m.p. 130.5° C. to 132° C.
m-iodobenzoate of 5α-cholestanol
m-iodobenzoate of 5α-5,6-dihydrositosterol
m-iodobenzoate of 7α-cholestanol
m-iodobenzoate of 7α-5,6-dihydrositosterol
p-iodophenylacetate of 5α-cholestanol
p-iodophenylacetate of 5α-5,6-dihydrositosterol
p-iodophenylpropionate of 5α-cholestanol
p-iodophenylpropionate of 5α-5,6-dihydrositosterol
p-iodophenylacetate of 6β-cholestanol
p-iodophenylacetate of 6β-5,6-dihydrositosterol

EXAMPLE II

Substitution of Chlorine

Meta-Iodobenzoate of 17α-Chloro-7α-Cholestanol

A: With phenyliododichloride

A solution of the m-iodobenzoate of 7α-Cholestanol (5α-cholestane-7α-ol) is prepared by dissolving 618 mg (1.0 mmol) of the m-iodobenzoate in 100 ml of methylene chloride together with 1.2 equivalents of phenyliododichloride. The solution is irradiated with a standard GE 275 W sunlamp at 25° C. for 30 minutes under nitrogen. The solvent is removed on a rotary evaporator, and traces of iodine are removed by addition and evaporation of carbon tetrachloride. The desired product remains as a residue.

B: With sulfuryl chloride

A solution (0.01 M) of the m-iodobenzoate of 7α-cholestanol, 1.1 equivalent of sulfuryl chloride and 10 mol percent of benzoyl chloride in methylene chloride is prepared. It is heated at 70° C. for 6 hours, and the solvent removed as described above to leave the desired product.

C: With chlorine

A solution of the m-iodobenzoate of 7α-cholestanol (3.7 g) and 1.2 molar equivalents of chlorine in 700 ml of carbon tetrachloride is prepared. The solution is irradiated with a sunlamp for 45 minutes at 25° C. and the solvent removed as described above to leave the desired product.

The following compounds are prepared by the above methods:
m-iodobenzoate of 9α-chloro-3α-cholestanol
m-iodobenzoate of 9α-chloro-3α-5,6-dihydrositosterol
p-iodophenylacetate of 14β-chloro-3α-cholestanol
p-iodophenylacetate of 14β-chloro-3α-5,6-dihydrositosterol
m-iodophenylacetate of 14β-chloro-3α-cholestanol
m-iodophenylacetate of 14β-chloro-3α-5,6-dihydrositosterol
m-iodophenylpropionate of 14β-chloro-3α-cholestanol
m-iodophenylpropionate of 14β-chloro-3-α-5,6-dihydrositosterol
4'-iodo-3-biphenylcarboxylate of 17α-chloro-3α-cholestanol
4'-iodo-3-biphenylcarboxylate of 17α-chloro-3α-5,6-dihydrositosterol
m-iodobenzoate of 14β-chloro-5α-cholestanol
m-iodobenzoate of 14β-chloro-5α-5,6-dihydrositosterol
m-iodobenzoate of 17α-chloro-7α-cholestanol
m-iodobenzoate of 17α-chloro-7α-5,6-dihydrositosterol
p-iodophenylacetate of 17α-chloro-5α-cholestanol
p-iodophenylacetate of 17α-chloro-3α-5,6-dihydrositosterol
p-iodophenylpropionate of 17α-chloro-5α-cholestanol p-iodophenylpropionate of 17α-chloro-5α-5,6-dihydrositosterol
p-iodophenylacetate of 20-chloro-6β-cholestanol
p-iodophenylacetate of 20-chloro-5β-5,6-dihydrositosterol

EXAMPLE III

Simultaneous Hydrolysis and Dehydrochlorination of Products of Example II

In each case, the residue is taken up in a mixture of 15 ml methanol containing 10% KOH and 15 ml dioxane. The solution is then heated at 80° for 1 hour and the solvent evaporated. 100 ml of saturated brine solution are added, and 5 extractions are performed with 100 ml portions of ether. The organic layer is dried (MgSO$_4$) and evaporated to afford the product unsaturated alcohol contaminated with some saturated alcohol from unreacted starting material. The alcohol is acetylated with 2 ml acetic anhydride and 2 ml pyridine in 20 ml dry benzene at 80° for 10 hours. The solvent is evaporated and the residue taken up in 200 ml of ether. This is then washed with 20 ml portions of 10% hydrochloric acid and then 10% sodium bicarbonate, dried (MgSO$_4$) and evaporated to afford the unsaturated acetates. Chromatography on silica gel containing 20% silver nitrate cleanly separates the unsaturated steroid from residual saturated material, and the acetates are then hydrolyzed with KOH in methanolic dioxane to afford the corresponding alcohols.

In this manner the following ols and their corresponding acetates are prepared:
9,10-dehydro-3α-cholestanol
9,10-dehydro-3α-5,6-dihydrositosterol
14,15-dehydro-3α-cholestanol
14,15-dehydro-3α-5,6-dihydrositosterol
16,17-dehydro-3α-cholestanol
16,17-dehydro-3α-5,6-dihydrositosterol
14,15-dehydro-5α-cholestanol
14,15-dehydro-5α-5,6-dihydrositosterol
20,22-dehydro-6β-cholestanol
20,22-dehydro-6β-5,6-dihydrositosterol
16,17-dehydro-7α-cholestanol
16,17-dehydro-7α-5,6-dihydrositosterol

EXAMPLE IV

Dehydrochlorination Without Hydrolysis

In each case the product of Example II is taken up in dry pyridine. The solution is heated at 80° C. for 2 hours and the solvent removed on a rotary evaporator.

The products prepared are:
meta-iodobenzoate of 9,11-dehydro-3α-cholestanol
meta-iodobenzoate of 9,11-dehydro-3α-5,6-dihydrositosterol
p-iodophenylacetate of 14,15-dehydro-3α-cholestanol
p-iodophenylacetate of 14,15-dehydro-3α-5,6-dihydrositosterol
meta-iodophenylacetate of 14,15-dehydro-3α-cholestanol
m-iodophenylacetate of 14,15-dehydro-3α-5,6-dihydrositosterol
meta-iodophenylpropionate of 14,15-dehydro-3α-cholestanol
meta-iodophenylpropionate of 14,15-dehydro-3α-dihydrositosterol
4'-iodo-3-biphenylcarboxylate of 16,17-dehydro-3α-cholestanol
4'-iodo-3-biphenylcarboxylate of 16,17-dehydro-3α-dihydrositosterol
meta-iodobenzoate of 14,15-dehydro-5α-cholestanol
meta-iodobenzoate of 14,15-dehydro-5α-5,6-dihydrositosterol
meta-iodobenzoate of 16,17-dehydro-7α-cholestanol
meta-iodobenzoate of 16,17-dehydro-7α-5,6-dihydrositosterol
p-iodophenylacetate of 16,17-dehydro-5α-cholestanol
p-iodophenylacetate of 16,17-dehydro-5α-5,6-dihydrosisterol
p-iodophenylpropionate of 16,17-dehydro-5α-cholestanol
p-iodophenylpropionate of 16,17-dehydro-5α-5,6-dihydrositosterol
p-iodophenylacetate of 20,22-dehydro-6β-cholestanol
p-iodophenylacetate of 20,22-dehydro-6β-dehydrositosterol The above products are hydrolyzed in methanolic dioxane containing potassium hydroxide as described in Example III to prepare the products of Example III.

EXAMPLE V

Formation of Ene-Adducts N-Phenyltriazolenedione Adduct

A solution of 16,17-dehydro-3α-cholestanol acetate, prepared as in Example III (1 g.) and 1.1 molar equivalent of N-phenyltriazolenedione in 100 ml of methylene chloride is allowed to stand at 25° C. for 24 hours. The solvent is removed on a rotary evaporator and the resulting ene-adduct isolated by chromatography on silica gel.

This procedure is utilized to prepare the corresponding ene-adduct of all of the compounds prepared in accordance with the procedure of Example III.

EXAMPLE VI

Reduction of Ene-Adducts

A total of 500 mg of a free ol-steroid prepared in accordance with the procedure of Example III is dissolved in 20 ml of ethylamine. Then 5 portions of 0.162 inch lithium wire (0.2 cm each portion) are added and the mixture stirred for 2 hours. The solution is filtered to remove excess lithium and the residue washed with ether. The solvents are evaporated at reduced pressure to leave the desired product as a residue.

The following compounds are prepared by this process. The compounds are identified as z-isomers on the basis of nmr spectrum and an analysis of the expected reaction mechanism.
17,20-dehydro-3α-cholestanol
17,20-dehydro-3α-5,6-dihydrositosterol
17,20-dehydro-5α-cholestanol
17,20-dehydro-5α-5,6-dihydrositosterol
17,20-dehydro-6β-cholestanol
17,20-dehydro-6β-5,6-dihydrositosterol; Nmr δ 1.55 as acetate
17,20-dehydro-7α-cholestanol
17,20-dehydro-7α-5,6-dihydrositosterol All are converted to acetates by reaction of the free hydroxyl group with acetic anhydride in pyridine for 3 hours at 80° C.

EXAMPLE VII

Oxidative Removal of Side Chain

For the removal of the side chain, 300 mg of an ester prepared in accordance with the previous example are taken up in 10 ml of ethyl acetate and treated with 3 equivalents of ozone at −15° C. for one hour. The excess ozone is removed by bubbling with oxygen and the resulting solution treated with excess dimethyl sulfide to decompose the ozonide. The resulting mixture is allowed to stand for 10 hours at 25° C. The desired product is isolated and purified by evaporation of the solvent and chromatography on silica.

The following compounds are prepared in accordance with this procedure.
Androsterone acetate
5α-androstane-5α-ol-17-one acetate
5α-androstane-6β-ol-17-one acetate
5α-androstane-7α-ol-17-one acetate

EXAMPLE VIII

Preparation of Dihydrocortisone Acetate

Chart V illustrates the use of the process of this invention for the preparation of dihydrocortisone acetate from cortexolone. It illustrates the application of the process of the invention to the pregnane series. Compound CCXVIII is the Bismethylenedioxy derivative of $\Delta^{9(11)}$-pregnene-3α,17α,21-triol-20-one. The characteristics of the compound as the acetate are: melting point 168.5°–169.5° C.; anal. carbon theoretical 69.41, found 69.33; hydrogen, theoretical 8.39, found 8.50. Compound CCXX is the bismethylenedioxy derivative of pregnene-17α,21-diol-3,11,20-trione. Its characteristics are as follows:

Melting point 215°–220° C.; anal. carbon, theoretical 68.29, found 68.15; hydrogen, theoretical 7.97, found 8.05.

EXAMPLE IX

Preparation of 9α-Fluoro Androsterone Acetate

Chart W illustrates the application of the process of the invention to the androstane series. It shows the conversion of androsterone acetate to the corresponding 9α-fluoro-11β-hydroxyl compound. This compound is readily converted by the procedure indicated on the chart to the known therapeutically active compound 9α-fluoro-17α-methyl-17β-hydroxy-5α-androstane-3,11-dione whose androgenic antiestrogenic and antigonadotrophin activity is described in U.S. Pat. No. 2,813,883.

Compounds prepared by the procedure of this invention and containing a 17-keto group are useful intermediates for the production of steroid hormones by procedures well known to those skilled in the art. Specifically, compounds with oxygen at the 3-position or the 3- and 5-position are useful since oxidation of the 3-hydroxyl group eliminates the 5-oxygen to produce the useful $\Delta^4$-3-one system. Compounds with oxygen at the 3- and 7-position are converted to useful intermediates by dehydration at carbon 7 to produce a double bond which can be further reduces. Those compounds with a 6-hydroxyl group may be similarly employed, that is, dehydrated and reduced.

The following table provides certain characterizing constants for many of the compounds shown in the charts.
XIX: m.p. 130.5°–132° C.
XXII: vinyl proton nmr at 5.3 delta
CCXVII: m.p. 242°–247° C.
CCXVI: m.p. 173°–174° C.
CCXIX: m.p. 180°–181° C.
CCXX: m.p. 215°–220° C.
We claim:

1. A method for substituting a chlorine atom for the tertiary hydrogen atom at the 9, 14, 17 or 20 position of a 3, 5, 6, 7 or 17-hydroxyl-5-α-steroid of the cholestan, androstane, or pregnane series which comprises producing an ester of the said hydroxy steroid with a carboxylic acid, acid chloride or acid anhydridge, esterifying agent carrying an iodoaryl group containing up to 12 aromatic carbon atoms and selected so that a chlorine atom covalently bonded to the iodine atom of the iodoaryl group is capable of approaching sufficiently close to the hydrogen atom to be replaced so that the internuclear distance between the said chlorine and hydrogen atoms is from 1.3 to 2.0 angstroms, and thereafter reacting the ester under free radical generating conditions with a molar excess of a halogenating agent selected from the group consisting of molecular chlorine, phenyliododichloride and sulfuryl chloride to replace the selected hydrogen with a chlorine atom; the esterified position, substituted hydrogen and ester being selected from the group consisting of:

| Esterified Position | Substituted Hydrogen | Ester |
| --- | --- | --- |
| 3α | 9 | m-iodobenzoate |
| 3α | 14 | p-iodophenylacetate |
| 3α | 14 | m-iodophenylacetate |
| 3α | 14 | m-iodophenylpropionate |
| 3α | 17 | 4'-iodo-3-biphenylcarboxylate |
| 5α | 14 | m-iodobenzoate |
| 5α | 17 | p-iodophenylacetate |
| 5α | 17 | m-iodophenylpropionate |
| 6β | 20 | p-iodophenylacetate |
| 7α | 17 | m-iodobenzoate |
| 17α | 9 | m-iodobenzoate |

2. A method as in claim 1 wherein the steroid is 3β-dihydrocholesterol, the esterifying reagent is 4'-iodo-3-biphenylcarboxylic acid and the hydrogen which is replaced is at the 17-αposition.

3. A method as in claim 1 wherein the steroid is 7α-cholestanol, the esterifying agent is m-iodobenzoyl chloride, and the hydrogen which is replaced is at the 17-αposition.

4. A method for the removal of a selected tertiary hydrogen atom at the 9, 14, 17 or 20 position of a 3, 5, 6, 7 or 17-hydroxyl-5α-steroid of the cholestane, androstane, or pregnane series which comprises producing an ester of the said hydroxy steroid with a carboxylic acid, acid chloride or acid anhydride esterifying agent carrying an iodoaryl group containing up to 12 aromatic carbon atoms and selected so that a chlorine atom covalently bonded to the iodine atom of the iodoaryl group is capable of approaching sufficiently close to the hydrogen atom to be removed so that the internuclear distance between the said chlorine and hydrogen atoms is from 1.3 to 2.0 angstroms, and thereafter;
   (1) reacting the ester under free radical generating conditions with a molar excess of a hologenating agent selected from the group consisting of molecular chlorine, phenyliododichloride and sulfuryl chloride to replace the selected hydrogen with a chlorine atom, and
   (2) dehydrochlorinating the resulting product;
the esterified position, removed hydrogen, and ester being selected from the gorup consisting of:

| Esterified Position | Removed Hydrogen | |
|---|---|---|
| 3α | 9 | m-iodobenzoate |
| 3α | 14 | p-iodophenylacetate |
| 3α | 14 | m-iodophenylacetate |
| 3α | 14 | m-iodophenylpropionate |
| 3α | 17 | 4'-iodo-3-biphenylcarboxylate |
| 5α | 14 | m-iodobenzoate |
| 5α | 17 | p-iodophenylacetate |
| 5α | 17 | m-iodophenylacetate |
| 6β | 20 | p-iodophenylacetate |
| 7α | 17 | m-iodobenzoate |
| 17α | 9 | m-iodobenzoate |

5. A method as in claim 4 wherein the steroid is 3β-dihydrocholesterol, the esterifying reagent is 4'-iodo-3-biphenylcarboxylic acid and the hydrogen which is removed is at the 17-αposition.

6. A method as in claim 4 wherein the steroid is 7α-cholestanol, the esterifying agent is m-iodobenzoyl chloride, and the hydrogen which is removed is at the 17-αposition.

7. The method of claim 1 including the further step of dehydrochlorination with simultaneous hydrolysis of the ester group which comprises reaction of the chlorinated steroid with a strong inorganic base selected from the group consisting of sodium, potassium and lithium hydroxide in a reaction inert polar organic solvent at a temperature of from 25° C. to 100° C. for from 0.5 to 5 hours.

8. The method of claim 1 including the further step of dehydrochlorination while leaving the ester group intact which comprises reaction of the chlorinated steroid with a weak organic or inorganic base selected from the group consisting of triethylamine, pyridine and sodium acetate, bicarbonate, carbonate or phosphate in a reaction inert polar organic solvent at 80° C. for from 0.5 to 6 hours.

9. The method of claim 4 wherein dehydrochlorination is effected with simultaneous hydrolysis of the ester group by reaction of the chlorinated steroid with a strong inorganic base selected from the group consisting of sodium, potassium and lithium hydroxide in a reaction inert polar organic solvent at a temperature of from 25° C. to 100° C. for from 0.5 to 5 hours.

10. The method of caim 4 wherein dehydrochlorination is effected while leaving the ester group intact by reaction of the chlorinated steroid with a weak organic or inorganic base selected from the group consisting of triethylamine, pyridine, and sodium acetate, bicarbonate, carbonate or phosphate in a reaction inert polar organic solvent at 80° C. for from 0.5 to 6 hours.

11. A method for the production of androsterone acetate which comprises the steps of:
(1) Esterifying 3β-dihydrositosterol with 4'-iodo-3-biphenylcarboxylic acid in the presence of triphenylphosphine and diethyl azodicarboxylate to produce the corresponding 3α-ester,
(2) Reacting resulting ester under free radical generating conditions with a molar excess of a hologenating agent selected from the group consisting of molecular chlorine, phenyliododichloride, and sulfuryl chloride to produce the corresponding 17β-chloro compound,
(3) Simultaneously dehydrochlorinating and hydrolyzing resulting compound with an alkaline reagent to form the corresponding 16,17-dehydro compound,
(4) Forming a 3α-acetate ester of the said dehydro compound by reacting with an acetylating agent,
(5) Forming an ene-adduct of said acetate by reaction with an enophile selected from the group consisting of N-phenyltriazolinedione, alkyl azodicarboxylic esters, each alkyl group containing up to six carbon atoms and hexafluorothioacetone,
(6) Reducing said ene-adduct to remove the enophile moiety,
(7) Acetylating resulting compound by reaction with an acetylating agent, and
(8) Oxidizing resulting compound to remove the side chain at the 17-position.

12. Meta-iodobenzoate of 3α-cholestanol.

13. Meta-iodobenzoate of 17β-chloro-7α-cholestanol.

14. 4'-Iodo-3-biphenylcarboxylate of 17α-chloro-3α-dihydrocholestanol.

15. Compounds of the class represented by the formulas:

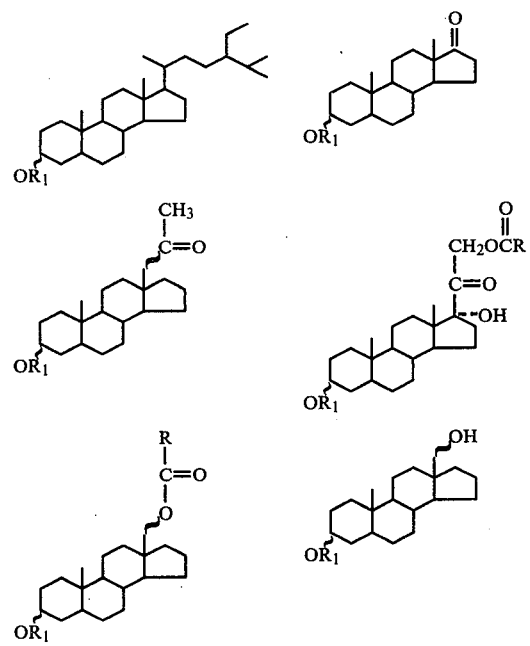

wherein $R_1$ is an iodoaryl substituted carboxylic ester group in which the iodoaryl moiety contains up to 12 aromatic carbon atoms and R is an alkyl group containing up to 5 carbon atoms.

16. Iodoaryl substituted esters of 3α-dihydrositosterol wherein the iodoaryl moiety is selected from the group consisting of m-iodobenzoyl, p-iodophenylacetyl, m-iodophenylacetyl, m-iodophenylpropionyl and 4'-iodo-3-biphenylcarboxyl.

17. A compound selected from the group consisting of those represented by the formula:

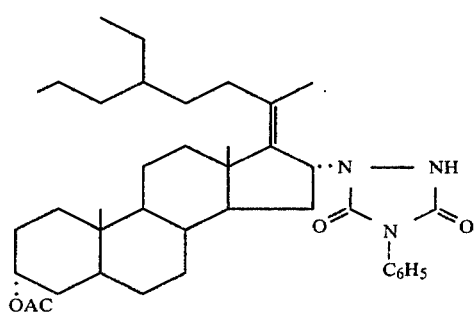
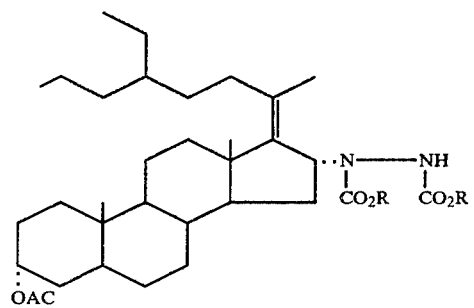
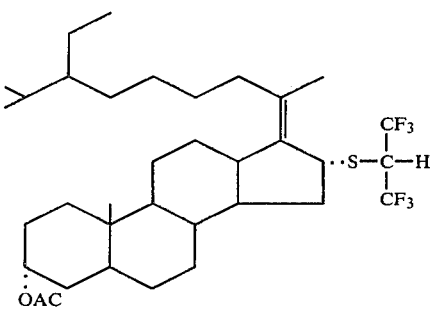
wherein R is an alkyl group containing up to six carbon atoms.
18. The 3α of 5,6-dehydrositosterol.
19. 17,20-Dehydro-6β-hydroxy-5,6-dihydrositosterol.
20. The bis methylenedioxy derivative of $\Delta^{9(11)}$-pregnane-3α,17α,21-triol-20-one.
21. The bis methylenedioxy derivative of pregnane-17α,21-diol-3,11-20-trione.
22. 16,17-Dehydrositosterol acetate.
23. 17,20-Dehydrositosterol acetate.
24. 17,20-Dehydrositosterol.
* * * * *